US007205284B2

United States Patent
Pasco et al.

(10) Patent No.: US 7,205,284 B2
(45) Date of Patent: Apr. 17, 2007

(54) POTENT IMMUNOSTIMULANTS FROM MICROALGAE

(75) Inventors: David Stanley Pasco, Oxford, MS (US); Nirmal Derek Pugh, Oxford, MS (US); Mahmoud ElSohly, Oxford, MS (US); Samir Ross, Oxford, MS (US); Nala Miazi ElSohly, Oxford, MS (US)

(73) Assignee: University of Mississippi, University, MS (US)

( * ) Notice: Subject to any disclaimer, the term of this patent is extended or adjusted under 35 U.S.C. 154(b) by 242 days.

(21) Appl. No.: 10/332,323

(22) PCT Filed: Jul. 10, 2001

(86) PCT No.: PCT/US01/21770

§ 371 (c)(1), (2), (4) Date: Feb. 3, 2003

(87) PCT Pub. No.: WO02/04000

PCT Pub. Date: Jan. 17, 2002

(65) Prior Publication Data

US 2007/0059317 A1 Mar. 15, 2007

Related U.S. Application Data

(60) Provisional application No. 60/217,001, filed on Jul. 10, 2001.

(51) Int. Cl.
*A61K 31/715* (2006.01)
*C08B 37/00* (2006.01)

(52) U.S. Cl. .................. 514/54; 536/55.1; 536/127; 536/123; 536/123.1; 536/124

(58) Field of Classification Search .............. 536/1, 536/3, 110, 55.1, 127, 123, 123.1, 124; 514/54
See application file for complete search history.

(56) References Cited

U.S. PATENT DOCUMENTS

| 3,462,412 | A |   | 8/1969  | Yamada et al.              |
|-----------|---|---|---------|----------------------------|
| 4,511,559 | A | * | 4/1985  | Szendrei et al. ..... 514/54 |
| 4,533,548 | A |   | 8/1985  | Umezawa et al.             |
| 4,786,496 | A |   | 11/1988 | Watanabe et al.            |
| 4,822,612 | A |   | 4/1989  | Shinpo                     |
| 4,831,020 | A | * | 5/1989  | Watanabe et al. ..... 514/54 |
| 5,089,481 | A | * | 2/1992  | Muto et al. ..... 514/54    |
| 5,385,832 | A | * | 1/1995  | Tuse et al. ..... 435/101   |
| 5,585,365 | A |   | 12/1996 | Hayashi et al.             |
| 6,207,652 | B1| * | 3/2001  | Sakai et al. ..... 514/54   |

OTHER PUBLICATIONS

Jensen et al., Consumption of Aphanizomenon flos-aque has Rapid Effects on the Circulation and Function of Immune Cells in Humans, JANA 2000 vol. 2, No. 3, pp. 50-58.*
Kay, R.A., Microalgae as Food and Supplement. Crit. Rev. Food Sci. Nutr. 1991 30(6)., pp. 555-573.*
Elsohly et al. U.S. Appl. No. 10/332,408, filed Aug. 13, 2003.*
ImmunosImmunostimulants—John W. Hadden, Immunology Today, vol. 14, No. 6 1993 pp. 275-280.
Immunomodulatory agents for prophylasix and therapy of infections—K. N. Masihi, International Journal of Antimicrobial Agents, pp. 181-191.
Immunotherapy and Cytokines—Kent R. Van Kampen, Seminars in Veterinary Medicine and Surgery, vol. 12, No. 3 Aug. 1997, pp. 186-192.
Polysaccharides in Pharmacy: Current Applications and Future Concepts—G. Franz—PlantaMedica, Feb. 6, 1989, pp. 493-497.
Immunomodulators—Michael O. Frank and Gerald L. Mandell, Basic Principles in the Diagnosis and Management of Infectious Diseases, pp. 450-458.
Wound healing: the role of marophages—Kathy Wilson, Nursing in Critical Care, vol. 2 1997 pp. 291-296.
The Effect of Acemannam Immunostimulant in Combination with Surgery and Radiation Therapy on Spontaneous Canine and Feline Fibrosarcomas—G. King, K. Yates, P. Greenlee, et al, Journal of the American Animal Hospital Association, pp. 439-447.
KRN7000 as a New Type of Antitumor and Immunostimulatory Drug—T. Natori, et al., Drugs from the Sea, pp. 86-87, Sep./Oct. 1995.
Recent Natural Products Based Drug Development: A Pharmaceutical Industry Perspetive—Yue-Zhong Shu, J. Nat. Prod. 1998, pp. 1053-1071.
*Spirulina*, the Edible Microorganism, O. Ciferri, Microbiological Reviews, Dec. 1983, pp. 551-578.

(Continued)

*Primary Examiner*—Shaojia Anna Jiang
*Assistant Examiner*—Devesh Khare
(74) *Attorney, Agent, or Firm*—Eugene C. Rzucidlo; Hunton & Williams LLP

(57) ABSTRACT

Immunostimulatory polysaccharides can be preferentially extracted from food-grade microalgae using an aqueous ethanol extraction procedure. The resulting preparations exhibit extremely potent immunostimulatory activity. The preferential extraction of these immunostimulatory polysaccharides is dependent on the concentration of ethanol used and the extraction temperature. The most efficient conditions are 50% ethanol concentration at temperatures between 60° and 70° C. The isolated polysaccharide preparations are potentially useful as a botanical or pharmaceutical preparation to improve immune function.

22 Claims, 11 Drawing Sheets

OTHER PUBLICATIONS

The Effects of *Chlorella Vulgaris* in the Protection of Mice Infected With *Listeria Mnocytogenes*. Role of Natural Killer Cells—Denise C. M. Dantas, et al, Immunopharmacology and Immunotoxicology 1991—pp. 609-619.

Effect of *Chlorella vulgaris* on bone marrow progenitor cells of mice infected with *Listeria monocytogenes*—Denise C. M. Dantas—Mary L.S. Queiroz, Int'l. Journal of Immunopharmacology 1999 pp. 499-508.

Dietary *Sprulina Platensis* Enhances Humoral and Cell-Mediated Immune Functions in Chickens—M. A. Qureshi et al., Immunopharmocol. Immunotoxical 1996 pp. 465-476.

The Macrophage—a cell for all seasons—N. Morrissette, E. Gold, A. Aderem—Cell Biology May 1999 pp. 199-201.

Evaluation of Chemoprevention of Oral Cancer With *Spirulina fusiformis*—B. Mathew et al, Nutrition and Cancer 1995 pp. 197-202.

Consumption of *Aphanizomenon flos-aquae* Has Rapid Effects on the Circulation and Function of Immune Cells in Humans—G. S. Jensen, et al, JANA vol. 2 Jan. 2000 pp. 50-58.

A New Type of Biological Response Modifier from *Chlorella vulgaris* Which Needs Protein Moiety to Show an Antitumour Activity—K. Noda, et al., Phytotherapy Research vol. 12 1998 pp. 309-319.

A Novel Glycoprotein Obtained from *Chlorella vulgaris* Strain CK22 Shows Antimetastatic Immunopotentiation—K. Tanaka, Cancer Immunol Immunother 1998 pp. 313-320.

A Water-Soluble Antitumor Glycoprotein From *Chlorella vulgaris*—K. Noda, et al, Planta Medica 1996 pp. 423-426.

Anti-Tumor-Promoting Glyceroglycolipids from the Green Algae, *Chlorella vulgaris*—T. Morimoto, et al, Phytochemistry vol. 40 1995, pp. 1433-1437.

Inhibition of tumor invasion and metastasis by calcium spirulan (Ca-SP), a novel sulfate polysaccharide derived from a blue-green alga, *Spirulina platensis*—T. Mishima, Clin. Exp., Metastasis 1998 pp. 541-550.

Further Purification and Structural Analysis of Calcium Sprulan from *Spirulina plantensis*—Jung-Burn Lee, et al, J. Nat. Prod. 1998, pp. 1101-1104.

Tumor-induced immune dysfunction: the macrophage connection—K. D. Elgert, et al, Journal of Leukocyte Biology—Sep. 1998 pp. 275-290.

The role of the macrophage in immune regulation—S. Gordon, Institut Pasteur 1998, pp. 685-788.

Molecular basis of macrophage activation: diversity and its origin—D.O. Adams & T.A. Hamilton, Oxford Press 1993 pp. 74-113.

Signal transduction through NF-kB—M.J. May and S. Ghosh, Feb. 1998, pp. 80-88.

Function and Activiation of NF-kB In the Immune System—P. A. Baeuerle & T. Henkel, Annual Review Inc., 1994 pp. 141-178.

Mechanism of expression and role in transcriptional control of the proto-oncognee NFKB-2/LYT-10, C C. Chang et al, Columbia University Sep. 10, 1993 pp. 923-933.

Isolation and Characterization of Patent Cell Walls and Cell Wall Components—W. S .York et al, Method in Enzymology 1985, pp. 3-41.

A Rapid Permethylation of Glycolipid, and Polysaccharide Catgalyzed by Methylsulfinyl Carbanion in Dimethyl Sulfoxide—S. I. Hakomori, The Journal of Biochemistry 1964, pp. 205-208.

The backbone of the pectic polysaccharide rhamnogalacturonan I is cleaved by an endohydrolase and an endolyase, P. Azadi et al, Oxford University Press, 1995 pp. 783-789.

Monosaccharides—R. J. Sturgeon, Method in Plant Biochemistry vol. 2, 1990.

High-Throughput RT-PCR Analysis of Multiple Transcripts Using a Microplate RNA Isolation Procedure—S. Su, et al BioTechniques Jun. 1997 pp. 185-190.

\* cited by examiner

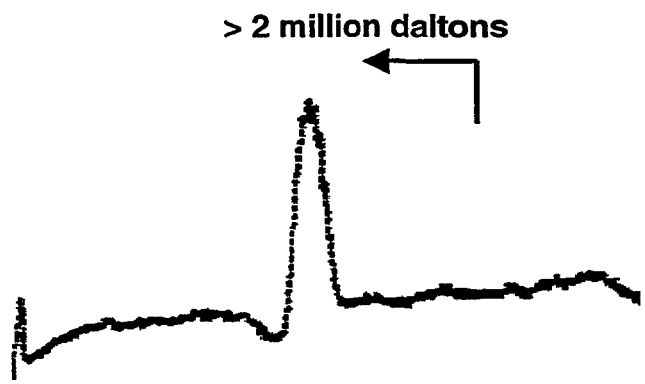
Fig. 1. Size exclusion HPLC chromatogram of polysaccharide preparation NP16847 (Example 1), 75µL injection at 500µg/mL.

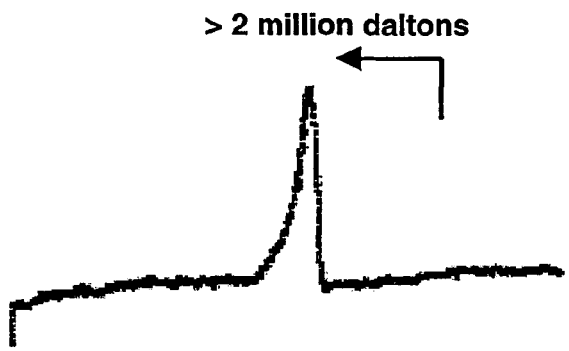
Fig. 2. Size exclusion HPLC chromatogram of polysaccharide preparation NP16848 (Example 2), 200μL injection at 125μg/mL.

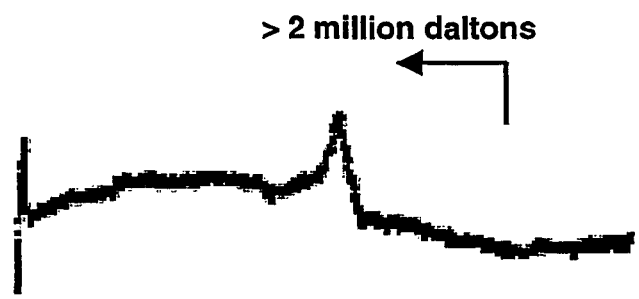
Fig. 3. Size exclusion HPLC chromatogram of polysaccharide preparation NP16846 (Example 3), 200μL injection at 35μg/mL.

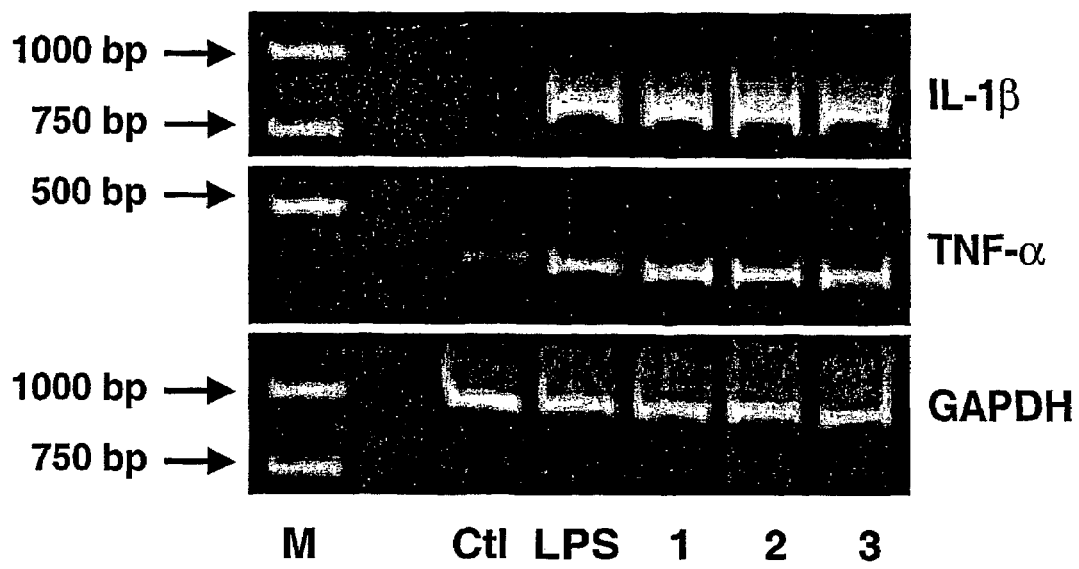

Fig. 4. Microalgal polysaccharide preparations NP16847, NP16848 and NP16846 enhance proinflammatory cytokine mRNA production. RT-PCR results for IL-1β mRNA, TNF-α mRNA and GAPDH mRNA in THP-1 cells at 2 hours: control, bacterial LPS at 10μg/mL, (1) polysaccharide preparation NP16847 (Example 1) at 0.5μg/mL, (2) polysaccharide preparation NP16846 (Example 3) at 0.5μg/mL, and (3) polysaccharide preparation NP16848 (Example 2) at 0.5μg/mL.

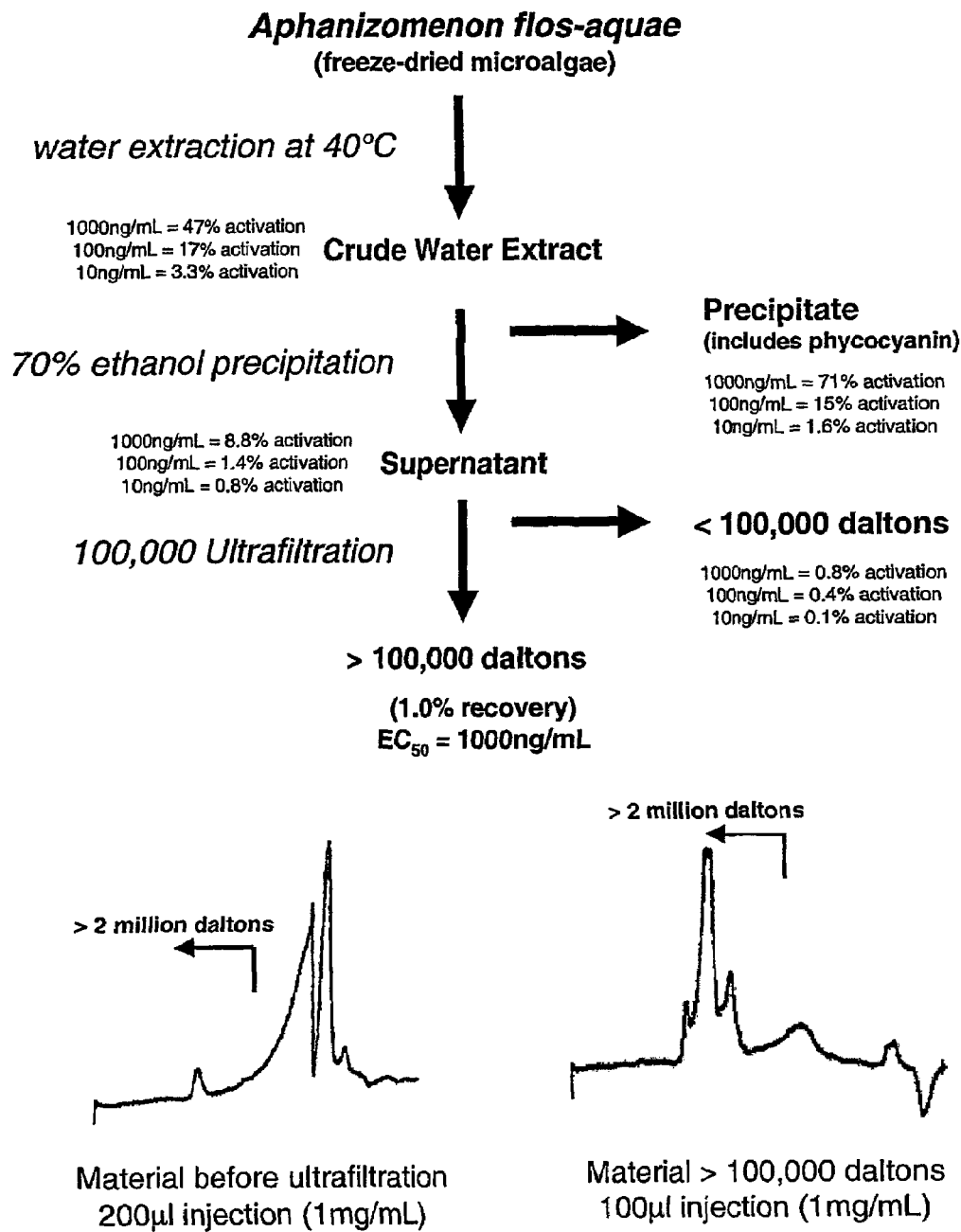
Fig. 5. Flow chart showing protocol for hot water extraction at 40°C followed by 70% ethanol precipitation to remove phycocyanin material (Example 4).

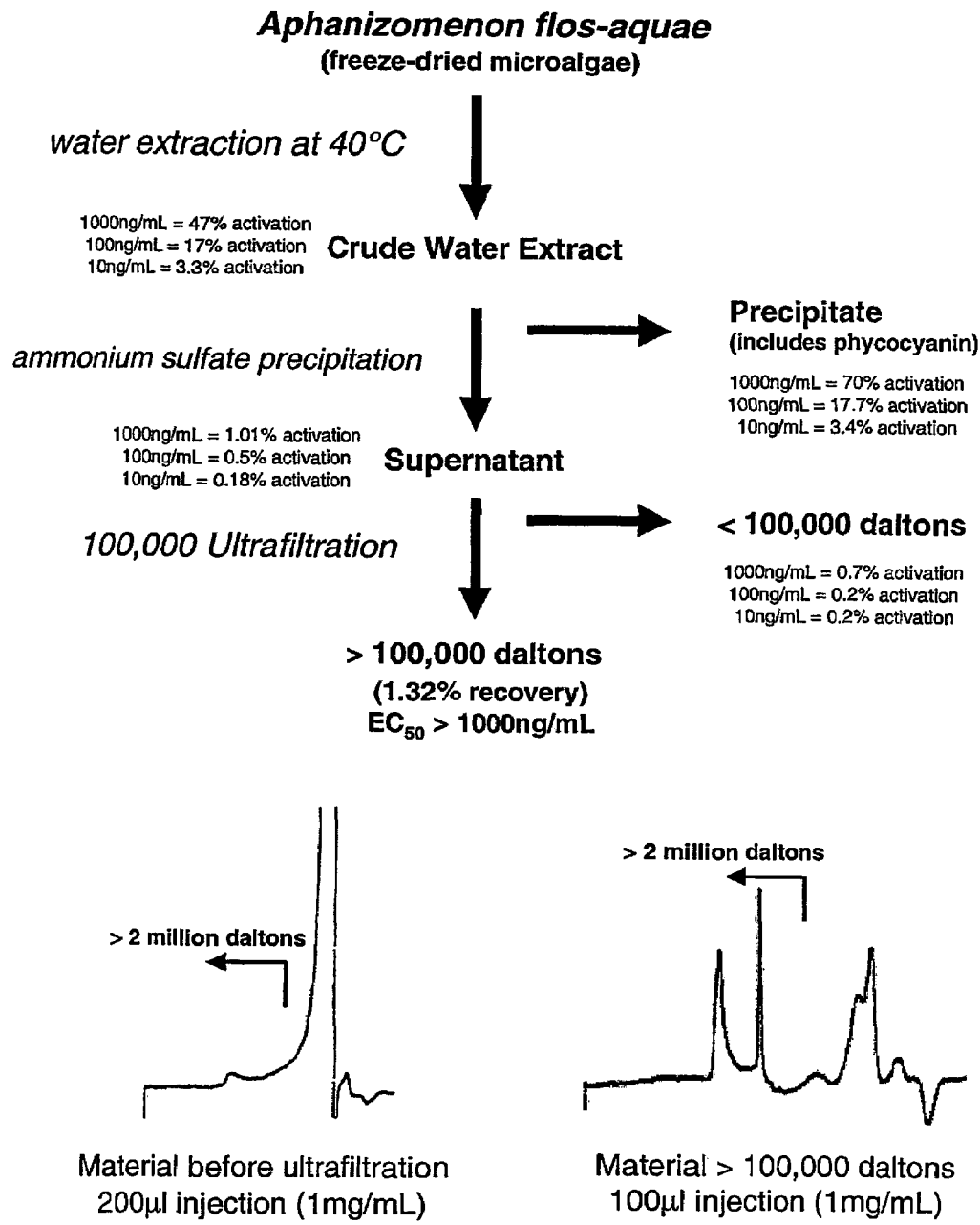
Fig. 6. Flow chart showing protocol for hot water extraction at 40°C followed by ammonium sulfate precipitation to remove phycocyanin material (Example 5).

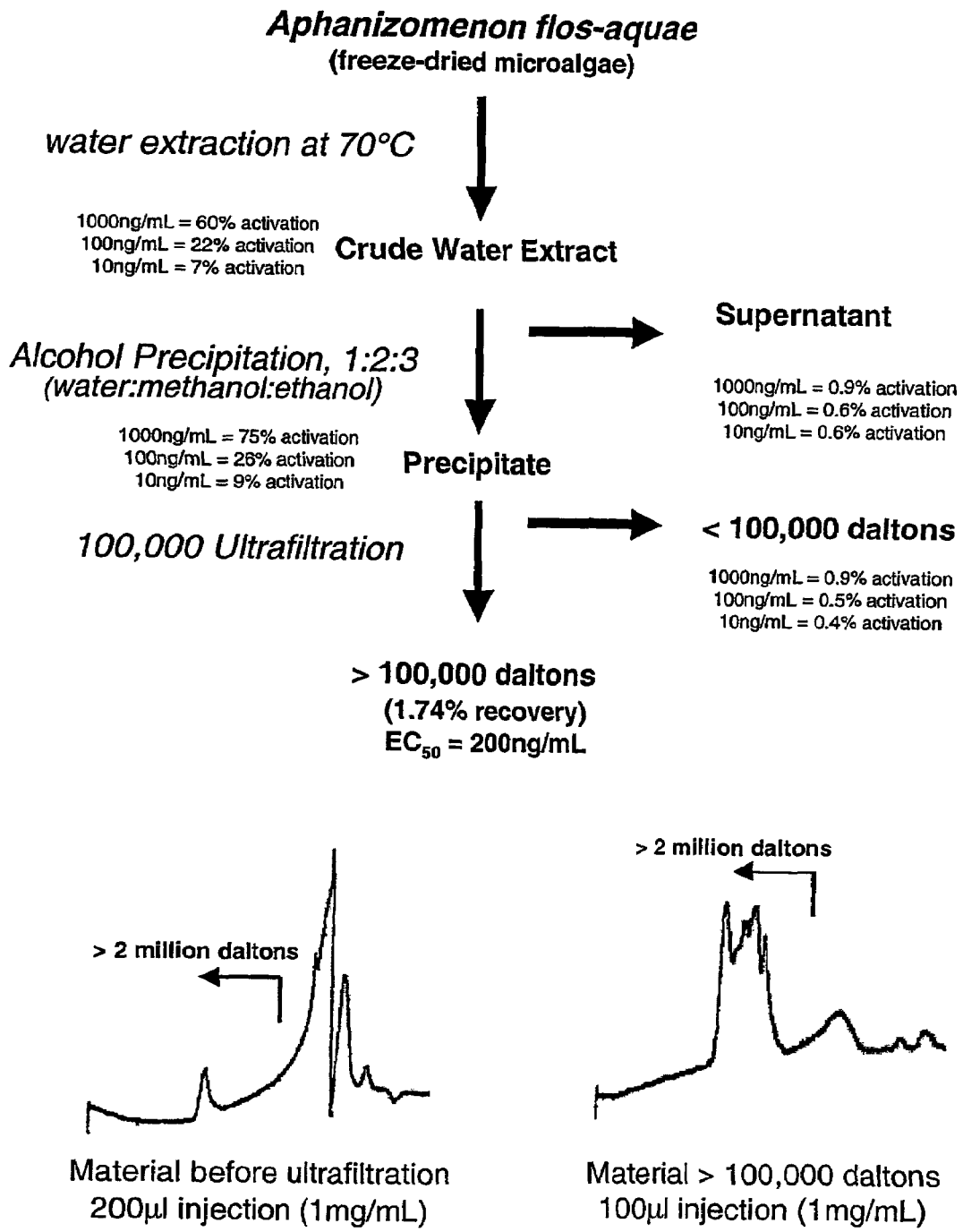
Fig. 7. Flow chart showing protocol for hot water extraction at 70°C (Example 6).

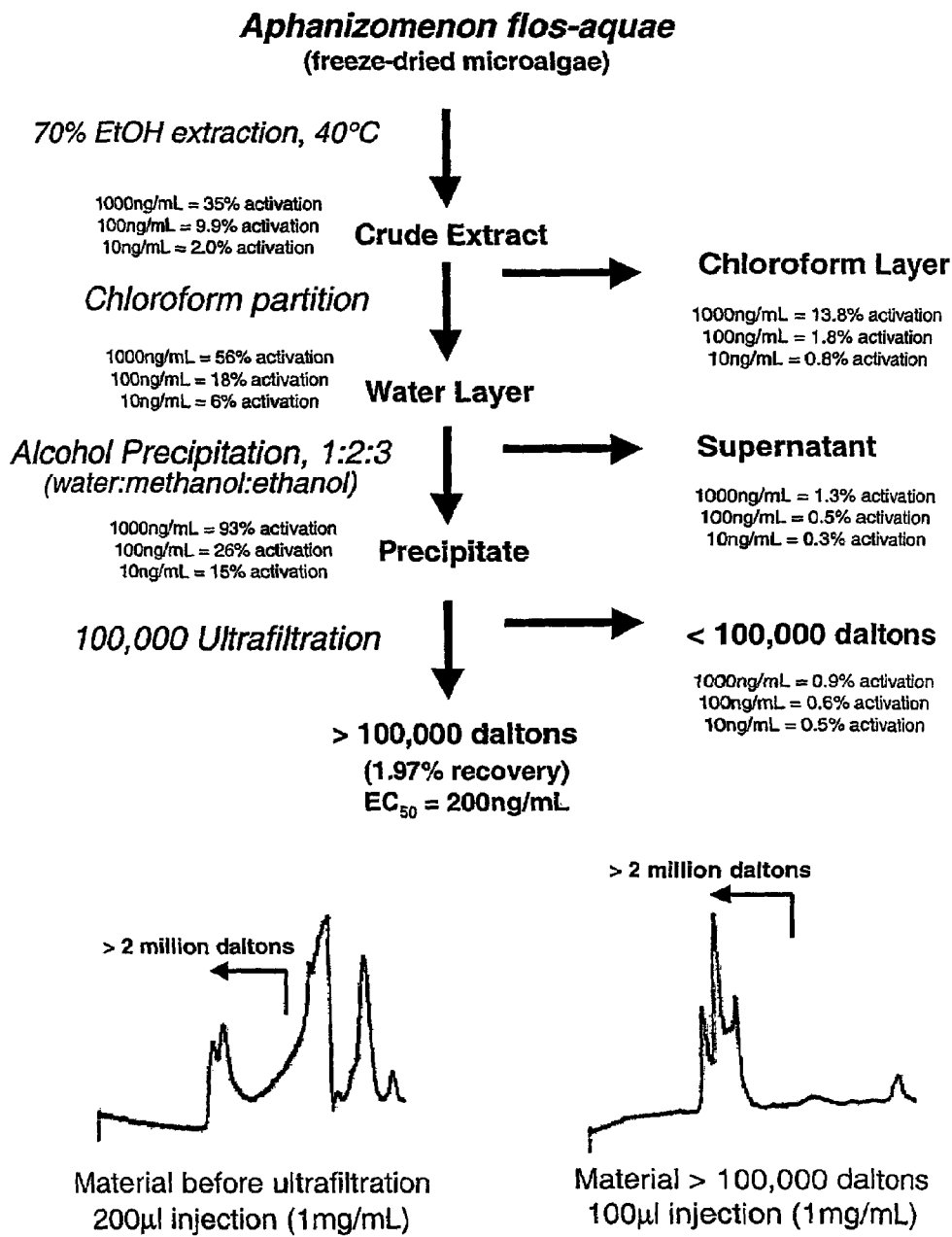
Fig. 8. Flow chart showing protocol for 70% ethanol extraction at 40°C without butanol partition (Example 7).

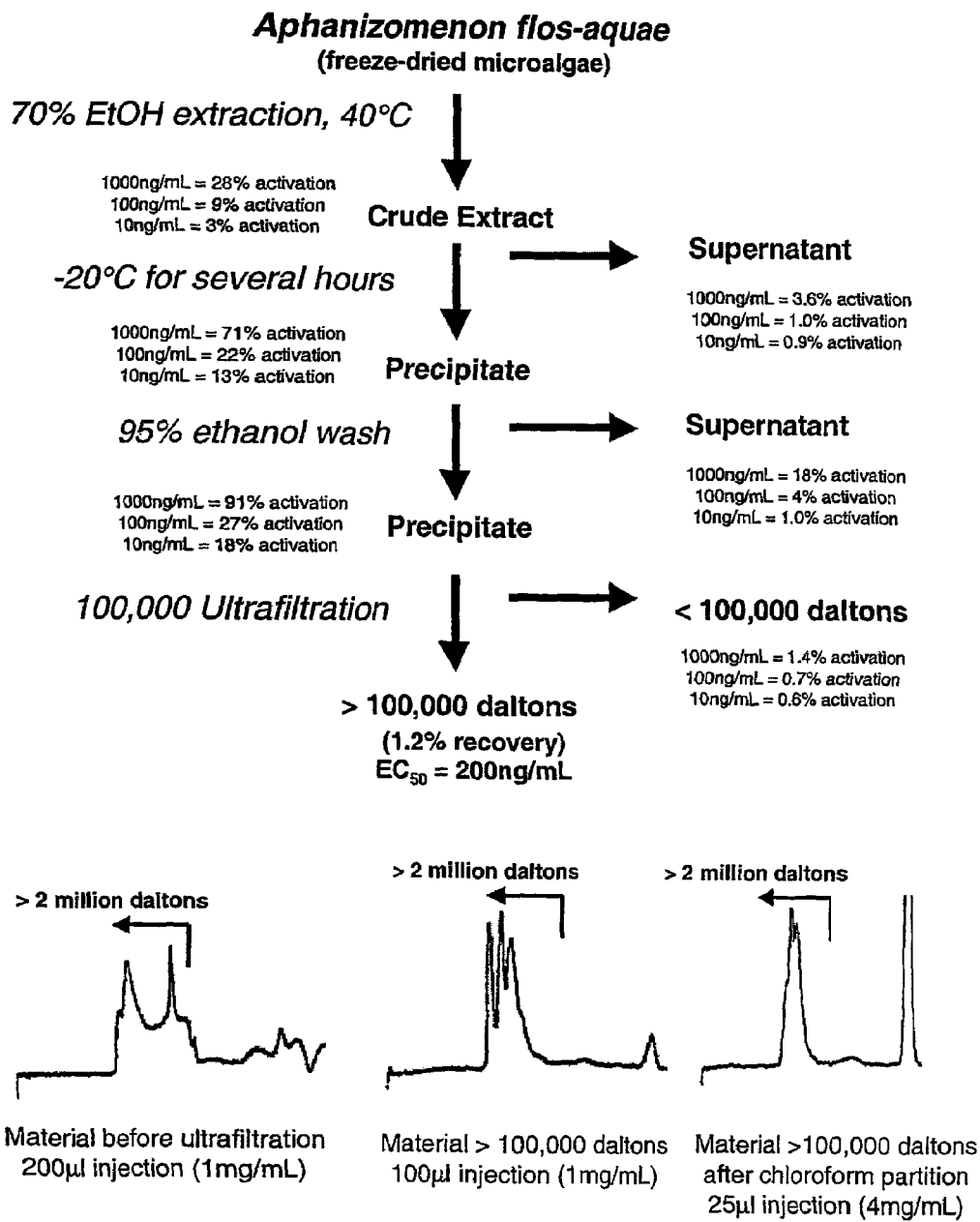
Fig. 9. Flow chart showing protocol for 70% ethanol extraction at 40°C followed by direct ethanol precipitation (Example 8).

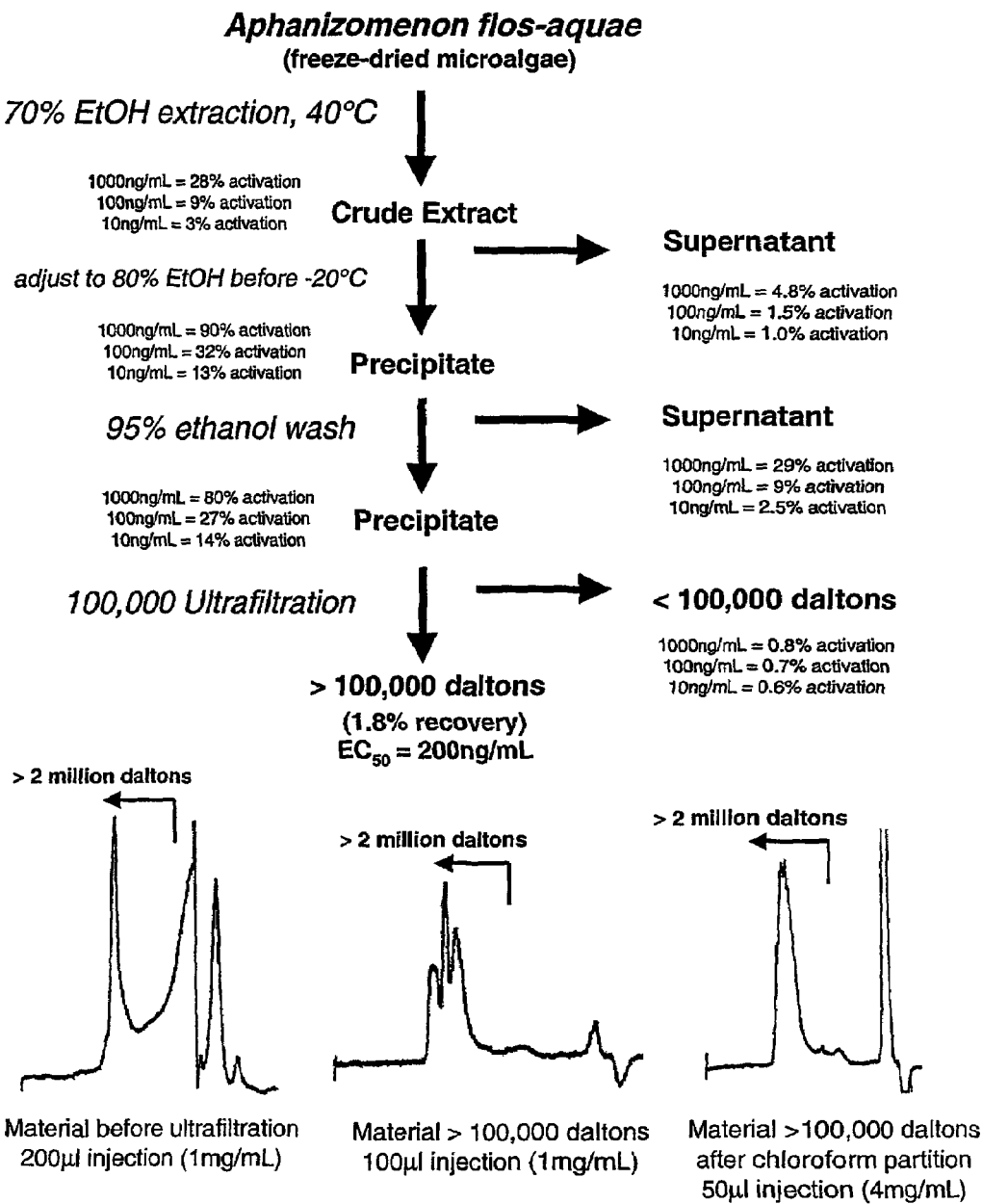
Fig. 10. Flow chart showing protocol for 70% ethanol extraction at 40°C followed by direct 80% ethanol precipitation (Example 9).

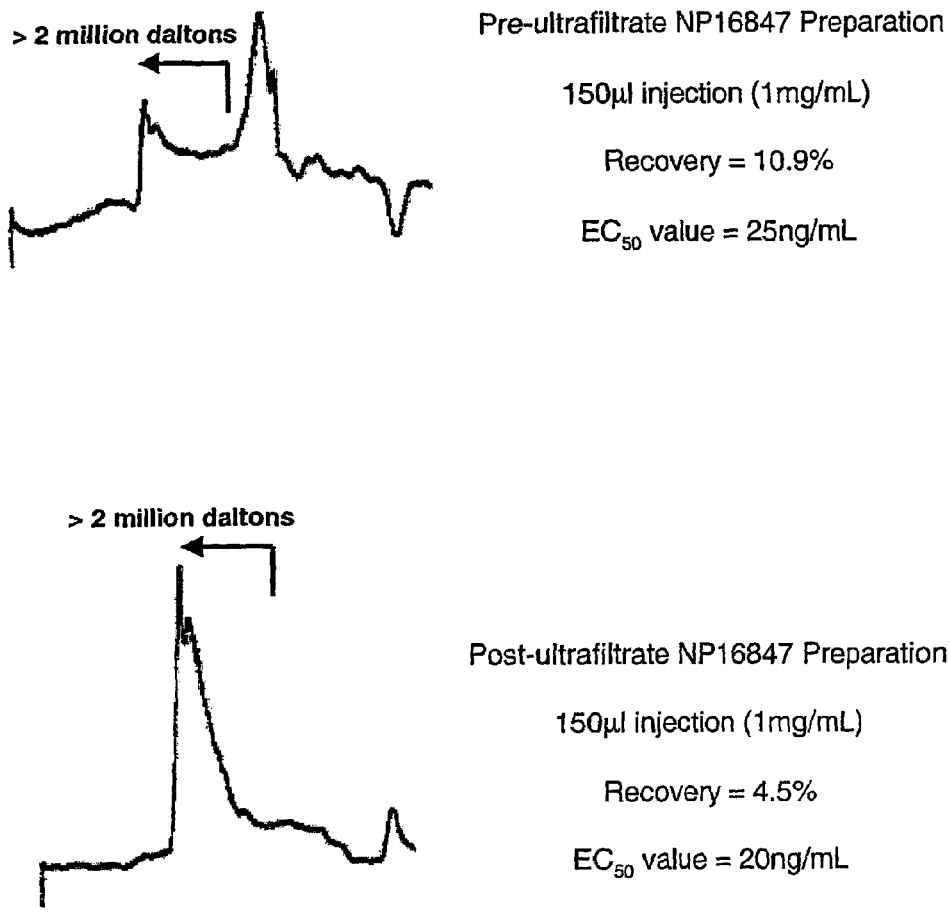
Fig. 11. SEC HPLC analysis of pre- and post-ultrafiltrate NP16847 preparations using optimal extraction conditions of 50% ethanol/60°C (Example 24).

POTENT IMMUNOSTIMULANTS FROM MICROALGAE

CROSS-REFERENCE TO RELATED APPLICATIONS

This application claims priority from U.S. Provisional Application Ser. No. 60/217,001, filed Jul. 10, 2001, the contents of which are incorporated by reference herein.

FIELD OF THE INVENTION

The present invention relates to a method for the extraction of immunostimulatory polysaccharide preparations from food-grade microalgae. It further relates to the identification of the structurally complex immunostimulatory water-soluble polysaccharide preparations isolated from food-grade microalgae containing active polysaccharides having an apparent molecular weight above 2 million daltons. It also relates to methods for the treatment and/or prevention of a variety of disease conditions using the preparations of this invention.

BACKGROUND OF THE INVENTION

During the past three decades immunotherapy has become an important approach for treating human diseases and conditions through the use of regimens designed to modulate immune responses. This is particularly important in pathological conditions where the immune system becomes compromised. Studies conducted in disease models and clinical trials demonstrate that augmenting host defense mechanisms is useful in treatment and prophylaxis against microbial infections, immunodeficiencies, cancer, and autoimmune disorders (1–5). Immune enhancing protocols may also have utility for promoting wound healing. In the process of wound healing, macrophages exhibit a principal role by modulating cellular proliferation and new tissue formation/regeneration. They also function as phagocytes, debridement agents and produce growth factors that influence the angiogenesis stage of wound repair (6).

Historically, the first immunostimulants developed were bacterial products (lysates and crude fractions), attenuated microbes or heat-killed bacteria. These included agents such as bacille Calmette-Guerin (BCG), *Corynebacterium parvum*, and lipopolysaccharide (1, 2). Although these agents have had limited success due to toxicities and side-effects, many have been licensed by the USDA for immunomodulation in veterinary medicine (3). Other substances have been developed from various sources and include those of natural origin, those derived by chemical synthesis or those synthesized using recombinant technologies. Most immunostimulants of natural origin are high molecular weight polysaccharides, glycoproteins or complex peptides (1). For example, three fungal polysaccharides derived from *Schizophyllum commune* (schizophyllan), *Lentinus edodes* (lentinan) and *Coriolus versicolor* (krestin) are currently in clinical use in Japan as biological response modifiers (4). Another polysaccharide, acemannan (isolated from *Aloe vera*), is licensed by the United States Department of Agriculture for the treatment of fibrosarcoma in dogs and cats (7). There are a few small molecular weight immunostimulants derived from natural products such as the glycosphingolipid KRN-7000. A clinical trial using KRN-7000 as an immunostimulant for treatment of solid tumors is currently in progress (8). Several immunostimulants of synthetic origin also have been developed that include compounds like isoprinosine and muramyl peptides (2). Recently a number of other immunomodulators of endogenous origin have been developed using recombinant technologies that have gained FDA approval. These agents include colony-stimulating factors, interferons and recombinant proteins (5). However, these compounds often have short half-lives and it is difficult to determine optimal dosage and appropriate combinations.

Although current immunostimulants show promise, there is still a need to develop more potent agents and increase the arsenal of available drugs for immunotherapy. One source of chemically diverse compounds that can be used for drug discovery of immunostimulants is natural products. For centuries natural products have been exploited as therapeutically useful agents, many of which are in clinical use today. Interest in natural products as a means to drug discovery is based on their unparalleled molecular diversity and rich spectrum of biological activities (9).

Since ancient times, microalgae have been used as a nutrient-dense food source. Historical records indicate that microalgae such as *Spirulina platensis* was consumed by tribes around Lake Chad in Africa and by the Aztecs living near Lake Texcoco in Mexico (10). During the last several decades there has been increasing interest in the commercial production of food-grade microalgae for human consumption and as feed for livestock. Among the various microalgae that have been explored for their commercial potential *Spirulina* species, *Chlorella* species and *Aphanizomenon flos-aquae* (AFA) are three major types that have been successfully produced and are in widespread use.

Both anecdotal reports and recent studies on the consumption of food-grade microalgae have reported enhanced immune function in both animals and humans. Oral administration of *Chlorella pyrenoidosa* has been correlated with enhanced natural killer cell activity (11) and granulocyte-macrophage progenitor cells (12) in mice infected with *Listeria monocytogenes*. Dietary *Spirulina platensis* increases macrophage phagocytic activity in chickens (13) and *Spirulina fusiformis* exhibits chemopreventive effects in humans (14). Human consumption of AFA has been reported to produce changes in immune cell trafficking and enhanced immune surveillance (15). The active components for all these effects have not been conclusively established.

Various compounds have been isolated from the microalgae studied herein. A number of polysaccharides and glycoproteins from *Chlorella* and *Spirulina* species have been characterized for their antitumor, antiviral and immunostimulating activity. In contrast, no such compounds showing any biological activity have been isolated from AFA.

A number of polysaccharides have been identified from *Chlorella* species that possess biological activity. In U.S. Pat. No. 4,533,548 an acidic polysaccharide was isolated from *Chlorella pyrenoidosa* that exhibits antitumor and antiviral activity (16). The glycosyl composition for this polysaccharide was mostly rhamnose, with minor amounts of galactose, arabinose, glucose and glucuronic acid. Another polysaccharide, isolated from marine *Chlorella minutissima*, reported in U.S. Pat. No. 4,831,020, appears to have tumor growth-inhibiting effects. However, no molecular weight or glycosyl composition was reported (17).

In U.S. Pat. No. 4,786,496, the lipid fraction (glycolipid portion) of marine *Chlorella* species displayed antitumor properties (18). Several glycoproteins have also been isolated from *Chlorella* species. For example, U.S. Pat. No. 4,822,612 reported a 45,000 dalton glycoprotein that has anticancer effects (19). Various other glycoproteins (20–23) and glyceroglycolipids (24) that may have immunopotentiating and antitumor properties also have been reported in the scientific literature. None of these compounds are polysaccharides.

Several different types of polysaccharides that exhibit biological activity have been isolated from *Spirulina* species. For example, the sulfated polysaccharide calcium spirulan inhibits tumor invasion and metastasis (25). Calcium spirulan (molecular weight 74,600 daltons) is composed of rhamnose (52.3%), 3-O-methylrhamnose (32.5%), 2,3-di-O-methylrhamnose (4.4%), 3-O-methylxylose (4.8%), uronic acids (16.5%) and sulfate (26).

U.S. Pat. No. 5,585,365 discloses that an antiviral polysaccharide with a molecular weight between 250,000 and 300,000 daltons was isolated from *Spirulina* species using hot water extraction (27). This polysaccharide is composed of rhamnose, glucose, fructose, ribose, galactose, xylose, mannose, glucuronic acid and galacturonic acid. A number of other low molecular weight polysaccharides that range between 12,600 and 60,000 daltons recently have been isolated from *Spirulina* species (28–30).

One way to determine immunostimulatory activity is to use a biological assay involving macrophages. Monocytes/macrophages are found in practically every tissue of the body where they are critical in coordinating immune responses and numerous biological processes (31). They play a major role in phagocytosis, immune surveillance, wound healing, killing of microbes and tumor cells, and antigen presentation to T lymphocytes (32). In cancer, macrophages mediate tumor cytotoxicity functions through the production of cytokines and other immune factors (33). In order for macrophages to play a major role in adaptive and innate immunity they must respond effectively to environmental agents by first becoming activated (34). Macrophage activation is mediated by proinflammatory transcription factors such as nuclear factor kappa B (NF-kappa B). Such transcription factors then control and modulate the activation/repression of an array of genes that mediate a variety of immune responses.

In unstimulated macrophages, NF-kappa B exists as inactive heterodimers sequestered by inhibitory-kappa B (I-kappa B) proteins within the cytosol. Agents that cause I-kappa B proteins to dissociate and degrade allow for the translocation of NF-kappa B dimers to the nucleus where they can activate transcription of downstream genes (35). Target genes regulated by NF-kappa B include proinflammatory cytokines, chemokines, inflammatory enzymes, adhesion molecules and receptors (36).

In this invention a transcription factor based assay for NF-kappa B in human monocytes was used to guide extraction, isolation, characterization and development of immunostimulatory polysaccharide preparations from food-grade microalgae. The polysaccharides of the present invention are both water soluble and soluble in aqueous ethanol solution unlike almost all other polysaccharides now available.

SUMMARY OF THE INVENTION

Novel water-soluble polysaccharide preparations having macrophage immunostimulatory activity and containing active polysaccharides having apparent molecular weights above 2 million daltons were isolated from *Aphanizomenon flos-aquae* (AFA), *Chlorella pyrenoidosa*, and *Spirulina platensis*. The instant polysaccharide preparations are at least a thousand times more active for monocyte activation than polysaccharide preparations that are currently used clinically for immunotherapy in cancer patients.

According to one embodiment of the invention, immunostimulatory preparations are isolated from microalgae comprising polysaccharides extractable by a solvent comprising water or a mixture of water and at least one lower alkyl alcohol where the alkyl portion is from 1 to 4 carbon atoms and where the active polysaccharides have apparent molecular weights above approximately 2 million daltons. According to another embodiment, the immunostimulatory activity of the immunostimulatory preparation is manifested by monocyte/macrophage activation. According to another embodiment, the immunostimulatory preparation is extracted from the microalgae *Aphanizomenon flos-aquae*. According to another embodiment, the immunostimulatory preparation is extracted from the microalgae *Chlorella pyrenoidosa*. According to another embodiment, the immunostimulatory preparation is extracted from the microalgae *Spirulina platensis*. According to another embodiment, the glycosyl components of the active polysaccharides of the immunostimulatory preparation are substantially comprised of mannose, glucose, rhamnose, galactose, fucose, methylated sugars and N-acetylated amino sugars. According to another embodiment, the glycosyl components of the active polysaccharides of the immunostimulatory preparation are substantially comprised of arabinose, galactose, rhamnose, glucose and methylated sugars. According to another embodiment, the glycosyl components of the active polysaccharides of the immunostimulatory preparation are substantially comprised of rhamnose, glucuronic acid, fucose, galactose and methylated sugars. According to another embodiment, a pharmaceutical composition comprises any one of the previous immunostimulatory preparations and a pharmaceutically acceptable carrier or excipient. According to another embodiment, a dietary supplement comprises any one of the previous immunostimulatory preparations and an acceptable carrier or excipient for dietary supplements.

According to another embodiment, a method of enhancing immune function in an individual in need of such treatment, comprises administering to said individual an effective amount of the pharmaceutical composition or dietary supplement. According to another embodiment, the individual is suffering from a viral, bacterial or fungal infection. According to another embodiment, the individual is suffering from cancer. According to another embodiment, the individual is suffering from an immune deficiency. According to another embodiment, the individual is a human being. According to another embodiment, the individual is an animal.

According to another embodiment, a process to obtain a preparation from food-grade microalgae enriched for immunostimulatory polysaccharides, comprises the steps of: (a) producing an extract by extracting the microalgae with a solvent comprising water or a mixture of water and at least one lower alkyl alcohol where the alkyl portion is from 1 to 4 carbon atoms, wherein the alcohol concentration of the mixture ranges from 0–100% by volume at an extraction temperature of between about 4 degrees C. to 100 degrees C.; (b) optionally concentrating the extract to a small volume where a large volume makes a concentration step desirable; (c) precipitating the polysaccharide preparation out of the extract by precipitation means; (d) separating the precipitated polysaccharide preparation by separation means; and (e) washing the precipitate of (d) with 95% alcohol. According to another embodiment, the alcohol used in the extraction process to obtain a preparation from food-grade microalgae enriched for immunostimulatory polysaccharides is ethanol. According to another embodiment, the alcohol used in the extraction process to obtain a preparation from food-grade microalgae enriched for immunostimulatory polysaccharides is methanol. According to another embodiment, the alcohol used in the extraction process to obtain a preparation from food-grade microalgae enriched for immunostimulatory polysaccharides is isopropanol or propanol. According to another embodiment, the preferred alcohol concentration in step (a) is from 20–80%. According to another embodiment, the preferred temperature of extraction is between 40 and 80 degrees C. According to another embodiment, the process is used to obtain a preparation enriched for immunostimulatory polysaccharides from *Aphanizomenon flos-aquae*. According to another embodiment, the process is used to obtain a preparation enriched for immunostimulatory polysaccharides from *Chlorella pyrenidosa*. According to another embodiment, the process is used to obtain a preparation enriched for immunostimulatory polysaccharides from *Spirulina platensis*. According to another embodiment, the concentration step (b) is carried out (when needed) by evaporation of the solvent, preferably under reduced pressure. According to another embodiment, the concentration step (b) is carried out (when needed) by freeze drying. According to another embodiment, the concentration step (b) is carried out (when needed) by dialysis. According to another embodiment, the polysaccharide preparation is precipitated in step (c) by the addition of ethanol to a final concentration of about 80% ethanol. According to another embodiment, the polysaccharide preparation is precipitated in step (c) by cooling the extract. According to another embodiment, the polysaccharide preparation is precipitated in step (c) by the addition of a salt. According to another embodiment, the salt is ammonium sulfate. According to another embodiment, the precipitated polysaccharide preparation is separated in step (d) by filtration. According to another embodiment, the precipitated polysaccharide preparation is separated in step (d) by centrifugation. According to another embodiment, the precipitated polysaccharide preparation is washed in step (e) by 95% ethanol. According to another embodiment, the process further comprises purifying the precipitate by dissolving the precipitate in water and removing substantially all components of less than approximately 100,000 daltons molecular mass by ultra-filtration. According to another embodiment, the process further comprises purifying the precipitate by dissolving the precipitate in water and removing substantially all components of less than approximately 2 million daltons molecular mass by size exclusion column chromatography.

According to another embodiment, a method of treating an individual with an immunostimulatory polysaccharide preparation in order to provide to the individual a stimulation of monocyte/macrophage activity comprises administering to the individual an effective amount of a polysaccharide preparation extracted from food-grade microalgae in combination with an acceptable carrier. According to another embodiment, the immunostimulatory polysaccharide preparation is administered to enhance wound healing. According to another embodiment, the immunostimulatory polysaccharide preparation is administered to treat cancer. According to another embodiment, the immunostimulatory polysaccharide preparation is administered to treat immunodeficiency. According to another embodiment, the immunostimulatory polysaccharide preparation is administered to treat a viral, bacterial or fungal infection. According to another embodiment, the individual is a human being. According to another embodiment, the individual is an animal. According to another embodiment, a method of treating an individual with an immunostimulatory polysaccharide preparation in order to provide to the individual a stimulation of monocyte/macrophage activity comprises administering to the individual an effective amount of a polysaccharide preparation extracted from *Aphanizomenon flos-aquae* in combination with an acceptable carrier. According to another embodiment, a method of treating an individual with an immunostimulatory polysaccharide preparation in order to provide to the individual a stimulation of monocyte/macrophage activity comprises administering to the individual an effective amount of a polysaccharide preparation extracted from *Chlorella pyrenoidosa*. According to another embodiment, a method of treating an individual with an immunostimulatory polysaccharide preparation in order to provide to the individual a stimulation of monocyte/macrophage activity comprises administering to the individual an effective amount of a polysaccharide preparation extracted from *Spirulina platensis*.

BRIEF DESCRIPTION OF THE FIGURES

FIG. 1. Size exclusion HPLC chromatogram of polysaccharide preparation NP16847 (Example 1), 75 μL injection at 500 μg/mL.

FIG. 2. Size exclusion HPLC chromatogram of polysaccharide preparation NP16848 (Example 2), 200 μL injection at 125 μg/mL.

FIG. 3. Size exclusion HPLC chromatogram of polysaccharide preparation NP16846 (Example 3), 200 μL injection at 35 μg/mL.

FIG. 4. Microalgal polysaccharide preparations NP16847, NP16848 and NP16846 enhance proinflammatory cytokine mRNA production. RT-PCR results for IL-1β mRNA, TNF-α mRNA and GAPDH mRNA in THP-1 cells at 2 hours: control, bacterial LPS at 10 μg/mL, (1) polysaccharide preparation NP16847 at 0.5 μg/mL, (2) polysaccharide preparation NP16846 at 0.5 μg/mL, and (3) polysaccharide preparation NP16848 at 0.5 μg/mL.

FIG. 5. Flow chart showing protocol for hot water extraction at 40° C. followed by 70% ethanol precipitation to remove phycocyanin material (Example 4).

FIG. 6. Flow chart showing protocol for hot water extraction at 40° C. followed by ammonium sulfate precipitation to remove phycocyanin material (Example 5).

FIG. 7. Flow chart showing protocol for hot water extraction at 70° C. (Example 6).

FIG. 8. Flow chart showing protocol for 70% ethanol extraction at 40° C. without butanol partition (Example 7).

FIG. 9. Flow chart showing protocol for 70% ethanol extraction at 40° C. followed by direct ethanol precipitation (Example 8).

FIG. 10. Flow chart showing protocol for 70% ethanol extraction at 40° C. followed by direct 80% ethanol precipitation (Example 9).

FIG. 11. SEC HPLC analysis of pre- and post-ultrafiltrate NP16847 preparations using optimal extraction conditions of 50% ethanol/60° C. (Example 24).

DETAILED DESCRIPTION OF THE INVENTION

The transcription factor-based bioassay for activation of NF-kappa B in THP-1 human monocytes/macrophages was used to guide purification of the immunostimulatory polysaccharides and the optimization of their extraction. This assay measures immunostimulatory activity as indicated by increased expression of a NF-kappa B-driven luciferase reporter. THP-1 human monocytes (American Type Culture Collection, Rockville, Md.) were cultured in RPMI 1640 medium supplemented with fetal bovine serum (10% v/v) and amikacin (60 mg/L) at 37° C., under 5% $CO_2$ and 95% air. Actively growing cells were transiently transfected using DEAE-dextran (10 λg/1×10⁶ cells) and the pBIIXLUC reporter plasmid (1 µg/1×10⁶ cells). This plasmid, a gift from Dr. Riccardo Dalla-Favera, contains two copies of NF-kappa B motif from HIV/IgK (37). Transfection solution containing THP-1 cells was incubated for 7 minutes in a 37° C. water bath. The transfected cells were then resuspended in 10% FBS, RPMI 1640 medium and plated out in 96-well plates at a cell density of 2×10⁵ cells per well. After 24-hours, microalgae extracts, fractions and polysaccharide preparations were added to transfected cells. Cells were harvested and luciferase activity measured four hours after addition of samples. Cells were harvested using Packard filter plates and lysed using 30 µL of luciferase mix (1:1, LucLite™ luciferase:1×PBS, 1 mM Ca and Mg). LucLite™ luciferase reporter gene assay kit was purchased from Packard (Downers Grove, Ill.). Light emission was measured using a Packard microplate scintillation counter in single photon mode. Activation is reported as a percentage relative to maximal activation of NF-kappa B by 10 µg/mL LPS (*E coli*, serotype 026:B6, Sigma Chemical Co., St. Louis, Mo.) which was used as a positive control.

Glycosyl composition and glycosyl linkage analyses were performed by The University of Georgia, Complex Carbohydrate Research Center. The glycosyl composition was determined using GC-mass spectrometry analysis of the TMS-methyl glycosides. In order to identify the O-methylated sugars detected during the TMS-methyl glycoside procedure, glycosyl composition was also determined using the alditol acetate procedure (38). Glycosyl linkage analysis was performed using the Hakomori procedure (39), in combination with carboxyl-reduction in order to detect uronic acid linkages (40).

EXAMPLE 1

Initial Isolation of a High Molecular Weight Polysaccharide Preparation from AFA (NP16847) that Exhibits Potent Monocyte Activation Properties A crude extract from AFA (Lot No. 0110FA from Cell Tech, Klamath Falls, Oreg.), was prepared by extracting the freeze-dried material (125 g) three times (4 hours each) with 70% ethanol at 40° C. This crude extract had an $EC_{50}$ value of 10 µg/mL. Aqueous ethanol extracts were evaporated to dryness and then solvent partitioned between water and chloroform (1:1). The activity was found exclusively in the water layer which was further partitioned against n-butanol (water:n-butanol, 63:37). The more active water layer ($EC_{50}$=0.5 µg/mL) was subjected to alcohol precipitation (water:methanol:ethanol, 1:2:3) at −80° C. for 24 hours. This precipitated material, which is referred to as the pre-ultrafiltrate preparation, had an $EC_{50}$ value of 0.2 µg/mL and represents a recovery of 3% of dry AFA weight. This material was then passed through an ultrafiltration device with a 100,000 molecular weight cut-off polyethersulfone membrane (Centricon Plus-20 from Millipore, Bedford, Mass.). The retentate was subsequently washed several times with 3% KCl (w/v) to remove impurities that adhered (probably through ionic interaction) to the large molecular weight material. The retentate, which is referred to as post-ultrafiltrate material, had an $EC_{50}$ value of 0.1 µg/mL, representing a recovery of 0.6%.

The carbohydrate content of the post-ultrafiltrate NP16847 preparation was estimated to be between 90% and 100% using a colorimetric assay (41) with phenol-sulfuric acid at 450 nm and 490 nm. It is concluded from this result that this material is a preparation of polysaccharides. Elemental analysis performed by Galbraith Laboratories, Inc. (Knoxville, Tenn.) revealed that this material contains the following elements: 49.1% carbon, 40.8% oxygen, 7.62% hydrogen, 2.46% nitrogen and trace amounts of sulfur. Glycosyl composition and linkage analysis for the post-ultrafiltrate is presented in Table 1. NP16847 is comprised predominantly of mannose, glucose, 4-methyl mannose, rhamnose and methylated sugar residues along with other simple sugars and acetylated amino sugars. This is the first report of any polysaccharide isolated from AFA exhibiting any type of biological activity.

The post-ultrafiltrate NP16847 was analyzed using size exclusion chromatography (SEC). The set-up consisted of a Model 600E system controller, UK6 injector, Model 600 solvent delivery system, Model 401 differential refractometer and a Model 3396A Hewlett-Packard integrator. Analyses were performed at a flow rate of 1 mL/minute using HPLC grade water and a Shodex Ohpak KB-805 SEC column (300 mm length×8 mm ID) held at 30° C. This column is capable of separating molecules up to an estimated molecular weight of 4 million daltons. Analysis of post-ultrafiltrate NP16847 showed one peak that eluted in the void volume (FIG. 1) and had a retention time consistent with an apparent molecular weight of above 2 million daltons based on comparison with dextran standards.

The isolation procedure described in Example 1 for the purification of AFA polysaccharides is novel since the initial extraction uses 70% ethanol as compared with prior art procedures which employ hot water. To determine if this procedure could be used as a general method for the extraction of immunostimulatory polysaccharides from other food-grade microalgae, the procedure described in Example I was applied to two other microalgae commonly consumed as food supplements namely *Chlorella pyrenoidosa* and *Spirulina platensis*.

EXAMPLE 2

Initial Isolation of a High Molecular Weight Polysaccharide Preparation from *Chlorella pyrenoidosa* (NP16848) that Exhibits Potent Monocyte Activation Properties A crude extract from *Chlorella* (Lot No. VP0978 from Sun *Chlorella*, Torrance, Calif.), was prepared by extracting the freeze-dried material (35 g) three times (4 hours each) with 70% ethanol at 40° C. This crude extract had an $EC_{50}$ value of 25 µg/mL. Aqueous ethanol extracts were evaporated to dryness and then solvent partitioned between water and chloroform (1:1). The activity was found exclusively in the water layer which was further partitioned against n-butanol (water:n-butanol, 63:37). The more active water layer was subjected to alcohol precipitation (water:methanol:ethanol, 1:2:3) at −80° C. for 24 hours. The precipitate material was then passed through an ultrafiltration device with a 100,000 molecular weight cut-off polyethersulfone membrane (Centricon Plus-20 from Millipore, Bedford, Mass.). The retentate was subsequently washed several times with 3% KCl (w/v) to remove impurities that adhered (probably through ionic interaction) to the large molecular weight material. The post-ultrafiltrate material had an $EC_{50}$ value of 0.3 µg/mL, and represented a recovery of 0.2%.

The carbohydrate content of the post-ultrafiltrate NP16848 preparation was estimated to be between 90% and 100% using a colorimetric assay (41) with phenol-sulfuric acid at 450 nm and 490 nm. It is concluded from this result that this material is a preparation of polysaccharides. Glycosyl composition and linkage analysis for the post-ultrafiltrate is presented in Table 2. NP16848 is comprised predominantly of arabinose, galactose, rhamnose and methylated sugar residues along with other simple sugars and acetylated amino sugars. Although other immunostimulatory polysaccharides and water soluble preparations from *Chlorella* species have been reported in the literature, NP16848 is a novel composition.

The post-ultrafiltrate NP16848 analyzed using the HPLC size exclusion chromatography procedure described in Example 1 was found to contain one peak that eluted in the void volume (FIG. 2) and had a retention time consistent with an apparent molecular weight of above 2 million daltons based on comparison with dextran standards.

EXAMPLE 3

Initial Isolation of a High Molecular Weight Polysaccharide Preparation from *Spirulina platensis* (NP16846) that Exhibits Potent Monocyte Activation Properties A crude extract from *Spirulina* (Lot No. B16933 from Triarco Industries, Wayne, N.J.) was prepared by extracting the freeze-dried material (35 g) three times (4 hours each) with 70% ethanol at 40° C. This crude extract had an $EC_{50}$ value of 50 µg/mL. Aqueous ethanol extracts were evaporated to dryness and then solvent partitioned between water and chloroform (1:1). The activity was found exclusively in the water layer which was further partitioned against n-butanol (water:n-butanol, 63:37). The water layer was the more active and was subjected to alcohol precipitation (water:methanol:ethanol, 1:2:3) at −80° C. for 24 hours. The precipitate material was then passed through an ultrafiltration device with a 100,000 molecular weight cut-off polyethersulfone membrane (Centricon Plus-20 from Millipore, Bedford, Mass.). The retentate was subsequently washed several times with 3% KCl (w/v) to remove impurities that adhered (probably through ionic interaction) to the large molecular weight material. The post-ultrafiltrate material had an $EC_{50}$ value of 0.3 µg/mL, representing a recovery of 0.1%.

The carbohydrate content of the post-ultrafiltrate *Spirulina* preparation was estimated to be between 90% and 100% using a calorimetric assay (41) with phenol-sulfuric add at 450 nm and 490 nm. It is concluded from this result that this material is a preparation of polysaccharides. Glycosyl composition and linkage analysis for the post-ultrafiltrate is presented in Table 3. NP16846 is comprised predominantly of rhamnose, glucuronic acid, fucose, galactose and methylated sugar residues along with other simple sugars, uronic acids and acetylated amino sugars. Other polysaccharides with similar glycosyl compositions from *Spirulina* species have been reported in the literature but are much smaller in size than NP16846.

The post-ultrafiltrate NP16846 analyzed using the HPLC size exclusion chromatography procedure described in Example 1 was found to contain one peak that eluted in the void volume (FIG. 3) and had a retention time consistent with an apparent molecular weight of above 2 million daltons based on comparison with dextran standards.

Monocyte/Macrophage Activation

Messenger RNA (mRNA) levels of proinflammatory cytokines IL-1β and TNF-α were measured to confirm THP-1 monocyte/macrophage activation by microalgal polysaccharide preparations. The mRNA levels of GAPDH were also assayed as a control to determine the specificity of changes in IL-1β and TNF-α mRNA levels. Since GAPDH is a housekeeping gene, mRNA levels would be expected to remain constant unless changes were induced artifactually.

RT-PCR primers for IL-1β, TNF-α and GAPDH were purchased from Integrated DNA technologies, Inc. (Coralville, Iowa). Sequences for the primers were described in Su et al. (42). IL-1β forward (5'-ATG-GCA-GAA-GTA-CCT-AAG-CTC-GC-3'); IL-1β reverse (5'-ACA-CAA-ATT-GCA-TGG-TGA-AGT-CAG-TT-3'); TNF-α forward (5'-GAG-TGA-CAA-GCC-TGT-AGC-CCA-TGT-TGT-AGC-3'); TNF-α reverse (5'-GCA-ATG-ATC-CCA-AAG-TAG-ACC-TGC-CCA-GAC-T-3'); GAPDH forward (5'-TGA-AGG-TCG-GAG-TCA-ACG-GAT-TTG-GT-3'); GAPDH reverse (5'-CAT-GTG-GGC-CAT-GAG-GTC-CAC-CAC-3').

Actively growing THP-1 cells (3 mLs, 1×10⁶ cells/mL) were incubated for 2 hours in the presence of test material. Total RNA was isolated using the TRI Reagent® kit (Molecular Research Center, Inc., Cincinnati, Ohio) in which cells are lysed using a combination of phenol and guanidine thiocyanate. After the addition of bromochloropropane, RNA is separated into the aqueous phase and subsequently precipitated with isopropanol. Total RNA recovered using this method was about 30 µg. Electrophoresis of isolated RNA using 0.8% agarose gel showed no signs of contaminating DNA.

RT-PCR reactions were run using kit reagents from Promega (Madison, Wis.). Each reaction used the following components (total volume of 30 µL): 6 µL AMV/Tfl 5× reaction buffer, 0.6 µL dNTP mix (10 mM), 1.2 µL MgSO₄ (25 mM), 0.6 µL AMV reverse transcriptase (5 units/µL), 0.6 µL Tfl DNA polymerase (5 units/µL), 1.2 µL of each primer (15 pmol/µL), and 2 ng total RNA (IL-1β, TNF-α) or 5 ng total RNA (GAPDH). The RT-PCR protocol used a Techne Unit Progene automatic thermal cycler. First cycle consisted of 45 minutes at 48° C., followed by 2 minutes at 94° C. Amplification was achieved using 35 cycles: denature at 94° C. for 45 seconds, anneal at 60° C. for 1 minute, and extend at 68° C. for 2 minutes. The final cycle held samples at 68° C. for 7 minutes. Electrophoresis of RT-PCR products (mRNA IL-1β, TNF-α and GAPDH) was accomplished using 12 µL of reaction mix on 5% polyacrylamide gels with ethidium bromide used as the staining agent.

Treatment of THP-1 cells with either LPS or microalgal polysaccharide preparations resulted in a dramatic increase in both IL-1β mRNA (810 bp) and TNF-α mRNA (444 bp), as compared with the control. The mRNA levels of the housekeeping gene glyceraldehyde phosphate dehydrogenase (GAPDH, 1000 bp) was the same for all samples (FIG. 4).

The observed NF-kappa B activation by NP16847, NP16848, and NP16846 was not due to endotoxin contamination of the preparations. This was confirmed by the results of the following two experiments which were conducted to address this possibility. First, polymyxin B (10 µg/mL, Sigma Chemical Co., St. Louis, Mo.) was added in combination with each polysaccharide preparation (0.1 to 1 µg/mL) to observe whether there was any abrogation in NF-kappa B activation. Polymyxin B is a polycationic antibiotic known to block many of the biological effects of LPS by binding to the lipid A portion of the molecule. All three microalgal polysaccharide preparations were insensitive to polymyxin B addition (data not shown). Addition of polymyxin B to LPS (10 µg/mL) suppressed NF-kappa B activation by 75%. The second experiment used to examine possible endotoxin-mediated effects was to look for the presence of β-hydroxymyristate in the glycosyl composition analysis. There was no detectable levels of β-hydroxymyristate in sample preparations of NP16848 and NP16846. Thus, it is unlikely that the observed macrophage activation by NP16848 and NP16846 is due to endotoxins.

However, in two different sample preparations of NP16847 small amounts of β-hydroxymyristate (0.6% of total peak area) were detected. In order to determine how much "endotoxin-like" material was present, six samples of AFA were analyzed using the *Limulus amebocyte* lysate (LAL) assay (analysis performed by BioWhittaker, Walkersville, Md.). The amount of LAL positive material detected using this assay represented 0.002% of microalgal dry weight. By comparison, the percent recovery of NP16847 is about 300 times greater (0.6% of microalgal dry weight). This means that at the concentration required to produce half-maximal NF-kappa B activation by NP16847 (100 ng/mL), the total amount of potential LAL positive material present would be 300 pg/mL. This concentration of endotoxin would not be detectable using the macrophage assay system. Therefore, possible endotoxin contamination cannot account for the stimulatory effect of NP16847 on macrophage activation.

Examples 1 through 3 demonstrate that polysaccharide preparations with potent immunostimulatory activity are extractable from food-grade microalgae using 70% ethanol at 40° C. Subsequent steps in the isolation of these polysaccharide preparations involved a complex protocol and the use of organic solvents. Polysaccharides are traditionally extracted from natural sources using hot water due to their high water solubility. This hot water isolation procedure therefore would be expected to yield a higher percent recovery of these polysaccharides as compared to the initial extraction using 70% ethanol. In addition, since a hot water extract would be less likely to contain non-polar material, it would not be necessary to use organic solvent partitioning if this method proved successful. However, contrary to the predicted behavior, water extraction (Examples 4 through 6) gave preparations substantially less active than the procedure using the initial extraction with aqueous ethanol (Example 1) and also posed additional problems.

Both the HPLC size exclusion chromatographic analysis and immunostimulatory activity (macrophage activation) were measured as described in the earlier Examples. The microalgae used in each Example was freeze-dried AFA (Lot. 041900 Merc) obtained from Klamath Algae Products Inc., Klamath Falls, Oreg. Ultrafiltration (when used) was carried out using a device with a 100,000 molecular weight cut-off polyethersulfone membrane (Centricon Plus-20 from Millipore, Bedford, Mass.). For each experiment, the retentate material from ultrafiltration was washed several times with 3% KCl (w/v) to remove impurities that adhered (probably through ionic interaction) to the large molecular weight material.

EXAMPLE 4

40° C. Water Extraction and Phycocyanin Removal with Alcohol Precipitation

Water extraction of AFA at 40° C. was problematic because this crude extract contained a large amount of phycocyanin (a blue proteinaceous pigment). Attempts to remove phycocyanin by ultrafiltration were unsuccessful since this material was retained along with the NP16847 polysaccharide preparation in the 100,000-dalton molecular weight cut-off filter. Complete precipitation of the phycocyanin material by alcohol requires a solution of 70% ethanol or greater (data not shown). In order to evaluate this method, 10 g of freeze-dried AFA was extracted three times with water (62.5 mLs each time) at 40° C., between 4 and 8 hours each time. Crude water extract was lyophilized and redissolved in 40 mLs of water. Ethanol was added (92 mLs) at room temperature to achieve a final concentration of 70% ethanol. Perceptible materials (containing phycocyanin) were removed and the supernatant passed through an ultrafiltration device. The material at each step in the isolation procedure was evaluated for macrophage activation (FIG. 5). Clearly, the majority of the immunostimulatory activity was lost in the precipitate (also containing phycocyanin) during the 70% ethanol precipitation. The percent recovery of post-ultrafiltrate material (above 100,000 daltons) using this method was 1.0%. Although this percent recovery is higher than the 0.6% recovery of the post-ultrafiltrate obtained using the 70% ethanol extraction procedure of Example 1, this material contains other substances besides NP16847 since it had an $EC_{50}$ value of 1000 ng/mL. By comparison, the material from Example 1 has an $EC_{50}$ value of 100 ng/mL.

EXAMPLE 5

40° C. Water Extraction and Phycocyanin Removal with Ammonium Sulfate

Methods for the isolation of phycocyanin (43, 44) typically use an ammonium sulfate precipitation (40–65% saturation). This protocol was investigated to evaluate whether ammonium sulfate precipitation could selectively remove phycocyanin from the crude extract. Freeze-dried AFA (10 g) was extracted three times with water (62.5 mLs each time) at 40° C., between 4 and 8 hours each time. Crude water extract was lyophilized and redissolved in 40 mLs of water containing 48 g of ammonium sulfate (50% saturation). Perceptible materials (containing phycocyanin) were removed and the supernatant passed through an ultrafiltration device. The percent recovery of post-ultrafiltrate material was 1.32%, but probably contained little NP16847 since its specific activity was quite low ($EC_{50}$>1000 ng/mL). FIG. 6 summarizes the immunostimulatory activity of the material at each step in the isolation procedure. Similar to the previous approach, the majority of NP16847 was precipitated along with the phycocyanin by the addition of ammonium sulfate.

Clearly, the attempts to separate phycocyanin from NP16847 in the crude water extract were not successful. In addition, re-extraction of the marc material (leftover from the 40° C. water extraction) using aqueous ethanol at higher temperatures (e.g. 50% ethanol/60° C.) resulted in the isolation of a substantial amount of NP16847 (see Example 43). Thus, extracting with water at 40° C. did not provide a complete recovery of NP16847.

EXAMPLE 6

70° C. Hot Water Extraction

Water extraction at higher temperatures such as 70° C. would cause phycocyanin to denature and precipitate, leaving NP16847 and other polar molecules in solution. To evaluate this approach, 20 g of freeze-dried AFA was extracted three times with water (125 mLs each time) at 70° C., between 4 and 8 hours each time. This crude extract did not appear to contain any phycocyanin material as evidenced by the lack of blue color. The crude water extract was lyophilized and redissolved in 80 mLs of water. NP16847 was precipitated using alcohol (water:methanol:ethanol, 1:2:3) at −20° C. for 24 hours. Perceptible materials were passed through an ultrafiltration device. FIG. 7 summarizes the immunostimulatory activity of the material at each step in the isolation procedure. The $EC_{50}$ value for macrophage activation of the post-ultrafiltrate material (200 ng/mL) was slightly higher than the material obtained in Example 1 (100 ng/mL). The percent recovery of post-ultrafiltrate material obtained using this method was 1.74%, substantially higher than the 0.6% NP16847 recovery obtained from the 70% ethanol procedure of Example 1. Therefore extraction with 70° C. water recovers about 3 times as much NP16847 as indicated by the comparable $EC_{50}$ values of the post-ultrafiltrate materials.

Isolation of NP16847 using hot water extraction (at 70° C.) offers several advantages over the isolation procedure in Example 1. No organic solvents are used, only a few steps are required to obtain the final material, and about 3 times more NP16847 is extracted. However, there are several disadvantages. First, the crude water extract needs to be lyophilized in order to concentrate it to avoid excessively high volumes of alcohol in the precipitation. Second, the pre-ultrafiltrate contains a substantial amount of inactive material (as evidenced by a low $EC_{50}$ value of about 500 ng/mL and the HPLC chromatogram in FIG. 7) which results in a very slow purification using the ultrafiltration devices.

Several additional methods were evaluated based on modifications to the 70% ethanol extraction procedure described in Example 1. The following Examples describe isolation procedures where the use of organic solvents was not required and the isolation is accomplished in a limited number of steps. A simple, economic and efficient process was developed which overcame all problems associated with hot water extraction.

EXAMPLE 7

70% Ethanol Extraction at 40° C. with Chloroform Partitioning

For the extraction of NP16847 in Example 1, the second solvent partitioning step between n-butanol and water resulted in a substantial loss of immunostimulatory activity into the butanol layer. Therefore, the protocol in Example 1 was modified to remove the n-butanol solvent partition step. This new method is identical to the procedure in Example 1 except that there is only one solvent partition between chloroform and water (1:1). FIG. 8 summarizes the isolation scheme and immunostimulatory activity at each step in the isolation process. The $EC_{50}$ value for the post-ultrafiltrate material obtained using this method (200 ng/mL) was slightly higher than the material obtained in Example 1 (100 ng/mL). The percent recovery of post-ultrafiltrate NP16847 obtained using this procedure was 1.97%. Therefore, the removal of the butanol solvent partition step from the 70% ethanol extraction procedure (Example 1) enhanced recovery of post-ultrafiltrate NP16847 by over 3 times. However, the major disadvantage of this procedure is the use of chloroform in the organic solvent partition.

EXAMPLE 8

70% Ethanol Extraction at 40° C. and Direct Alcohol Precipitation

In order to evaluate an approach that skips both the butanol and chloroform partition, 10 g of freeze-dried AFA was extracted two times with 70% ethanol (125 mLs each time) at 40° C. The first extraction was for 3 hours and the second extraction was for 12 hours. Crude 70% ethanol extract was stored at −20° C. for several hours and perceptible material removed by centrifugation. Precipitate was washed with cold 95% ethanol (to remove remaining non-polar material), redissolved in water and then passed through an ultrafiltration device. FIG. 9 summarizes the immunostimulatory activity of the material at each step in the isolation procedure. $EC_{50}$ value of the post-ultrafiltrate material was slightly higher (200 ng/mL) as compared to the material obtained in Example 1 (100 ng/mL). The percent recovery of post-ultrafiltrate NP16847 was 1.2%. Although this yield is 2 times higher than that obtained using the extraction procedure described in Example 1, it is about 30% less than the recovery obtained using the protocol in Example 7. This lower yield is probably due to incomplete precipitation in 70% ethanol.

EXAMPLE 9

70% Ethanol Extraction at 40° C. and Direct 80% Alcohol Precipitation

The previous method (Example 8) was slightly modified to obtain a greater recovery of NP16847. The crude extract from the 70% ethanol extraction was adjusted to 80% ethanol by addition of cold 100% ethanol and stored at −20° C. for several hours. Perceptible material was processed the same as above. FIG. 10 summarizes the isolation scheme and immunostimulatory activity at each step in the isolation process. This modified method resulted in 5.7% recovery of pre-ultrafiltrate NP16847 preparation and an $EC_{50}$ value of 200 ng/mL in the monocyte activation assay. The percent recovery of post-ultrafiltrate material was 1.8%. $EC_{50}$ value for the post-ultrafiltrate material (200 ng/mL) was slightly higher than that observed for the material obtained in Example 1 (100 ng/mL), but identical to post-ultrafiltrate values obtained from Examples 6 and 7.

The procedure of direct precipitation of the NP16847 polysaccharide preparation from the crude 70% ethanol extract (Example 9) successfully achieves the original aims. No organic solvents (or methanol) are used, there is no lyophilization/solvent evaporation step, and only a few steps are required to obtain a relatively pure preparation of NP16847. A semi-pure preparation of NP16847 (70% of which is less than 100,000 daltons) can be obtained with elimination of the ultrafiltration purification step (refer to pre- and post-ultrafiltrate HPLC chromatograms in FIG. 10). This pre-ultrafiltrate NP16847 preparation would be sufficient for a dietary supplement (botanical) extract. Isolation of this material would simply require a direct alcohol precipitation from a crude 70% ethanol extract.

The following points summarize why this isolation procedure (Example 9) was superior to the others tested.

1. Water extraction at 40° C.
   a. Contains high levels of phycocyanin which cannot be separated from NP16847 by ultrafiltration or by ethanol or ammonium sulfate precipitation.

b. NP16847 obtained following ultrafiltration was of a low specific activity, $EC_{50}$~1000 ng/mL vs. 200 ng/mL (Example 9).
c. The marc material contained a substantial amount of NP16847 that could not be recovered using water extraction at this temperature (see Example 43).

2. Water extraction at 70° C.
a. Water extraction at this temperature contains excessive amounts of inactive polar material in the pre-ultrafiltrate. This is undesirable for two reasons. First, development of a pre-ultrafiltrate preparation would contain low levels of NP16847. Second, ultrafiltration is extremely slow to obtain a post-ultrafiltrate NP16847 preparation.
b. Although the procedure does not use toxic organic solvents it does require a lyophilization step of the crude extract.

3. 70% ethanol extraction followed by organic solvent partitioning.
a. Clearly the major disadvantage of this step is the use of an organic solvent (i.e. chloroform) to remove non-polar material.

From the examples described above, the optimum general procedure (Example 9) involves two initial extractions of freeze-dried AFA with 70% ethanol at 40° C. Crude extract is adjusted to 80% ethanol and cooled to −20° C. Precipitate is collected and washed with cold 95% ethanol to remove residual lipophilic material. The high molecular weight material (over 100,000 daltons), comprising ~30% of the pre-ultrafiltrate polysaccharide preparation, can be isolated using ultrafiltration. The following provides a comparison between the NP16847 preparation obtained in Example 9 and NP16847 prepared by extraction with 70% ethanol/40° C. (Example 1):

|  | NP16847 (Example 9) | NP16847 (Example 1) |
|---|---|---|
| Pre-ultrafiltrate Recovery | 5.7% | 3.0% |
| Pre-ultrafiltrate $EC_{50}$ value | 200 ng/mL | 200 ng/mL |
| Post-ultrafiltrate Recovery | 1.8% | 0.6% |
| Post-ultrafiltrate $EC_{50}$ value | 200 ng/mL | 100 ng/mL |

These data demonstrate that extracting AFA using the procedure in Example 9 results in 2 times more pre-ultrafiltrate and 3 times more post-ultrafiltrate NP16847. However, the $EC_{50}$ value of the post-ultrafiltrate preparation obtained by this procedure is slightly higher than that obtained from Example 1, indicating that some of the enhanced recovery is due to inactive material. Therefore, the conditions used in Example 9 were selected as a starting point for further optimization to improve the specific activity of the NP16847 preparation because of the following advantages that are offered by this new isolation method:

1. Optimal yield and good specific activity of both the pre- and post-ultrafiltration NP16847 polysaccharide preparations.
2. No toxic organic solvents are used.
3. No rotary evaporation or lyophilization of large volumes of water or solvent is involved.

Examples 10–38 provide a detailed analysis of changing both extraction temperature and ethanol concentration in order to optimize conditions used in Example 9.

EXAMPLE 10

70% Ethanol Extraction at 50° C. and Direct 80% Alcohol Precipitation

One g of freeze-dried AFA was extracted at 50° C. with 70% ethanol, first with 7.5 mLs for 3 hours and then with 6.25 mLs for 12 hours. Supernatants from both extractions were combined (11.2 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 6.5% recovery of pre-ultrafiltrate NP16847 preparation and an $EC_{50}$ value of 100 ng/mL in the monocyte activation assay (Table 4).

EXAMPLE 11

70% Ethanol Extraction at 60° C. and Direct 80% Alcohol Precipitation

One g of freeze-dried AFA was extracted at 60° C. with 70% ethanol, first with 7.5 mLs for 3 hours and then with 6.25 mLs for 12 hours. Supernatants from both extractions were combined (11.2 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 7.1% recovery of pre-ultrafiltrate NP16847 preparation and an $EC_{50}$ value of 100 ng/mL in the monocyte activation assay (Table 4).

EXAMPLE 12

70% Ethanol Extraction at 70° C. and Direct 80% Alcohol Precipitation

One g of freeze-dried AFA was extracted at 70° C. with 70% ethanol, first with 7.5 mLs for 3 hours and then with 6.25 mLs for 12 hours. Supernatants from both extractions were combined (11.4 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 7.1% recovery of pre-ultrafiltrate NP16847 preparation and an $EC_{50}$ value of 75 ng/mL in the monocyte activation assay (Table 4). Removal of low molecular weight material (<100,000 daltons) resulted in 2.7% recovery of post-ultrafiltrate NP16847 preparation and an $EC_{50}$ value of about 35 ng/mL.

EXAMPLE 13

70% Ethanol Extraction at 80° C. and Direct 80% Alcohol Precipitation

One g of freeze-dried AFA was extracted at 80° C. with 70% ethanol, first with 7.5 mLs for 3 hours and then with 6.25 mLs for 12 hours. Supernatants from both extractions were combined (11.2 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 7.6% recovery of pre-ultrafiltrate NP16847 preparation and an $EC_{50}$ value of 50 ng/mL in the monocyte activation assay (Table 4).

EXAMPLE 14

70% Ethanol Extraction at 23° C. and Direct 80% Alcohol Precipitation

One g of freeze-dried AFA was extracted at 23° C. with 70% ethanol, first with 7.5 mLs for 3 hours and then with 6.25 mLs for 12 hours. Supernatants from both extractions were combined (11.5 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 4.5% recovery of pre-ultrafiltrate NP16847 preparation and an $EC_{50}$ value of >250 ng/mL in the monocyte activation assay (Table 4).

EXAMPLE 15

60% Ethanol Extraction at 23° C. and Direct 80% Alcohol Precipitation

One g of freeze-dried AFA was extracted at 23° C. with 60% ethanol, first with 7.5 mLs for 3 hours and then with 6.25 mLs for 12 hours. Supernatants from both extractions were combined (11.3 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 7.0% recovery of pre-ultrafiltrate NP16847 preparation and an $EC_{50}$ value of >250 ng/mL in the monocyte activation assay (Table 4).

EXAMPLE 16

60% Ethanol Extraction at 40° C. and Direct 80% Alcohol Precipitation

One g of freeze-dried AFA was extracted at 40° C. with 60% ethanol, first with 7.5 mLs for 3 hours and then with 6.25 mLs for 12 hours. Supernatants from both extractions were combined (11.2 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 8.4% recovery of pre-ultrafiltrate NP16847 preparation and an $EC_{50}$ value of 200 ng/mL in the monocyte activation assay (Table 4).

EXAMPLE 17

60% Ethanol Extraction at 50° C. and Direct 80% Alcohol Precipitation

One g of freeze-dried AFA was extracted at 50° C. with 60% ethanol, first with 7.5 mLs for 3 hours and then with 6.25 mLs for 12 hours. Supernatants from both extractions were combined (11.0 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 9.4% recovery of pre-ultrafiltrate NP16847 preparation and an $EC_{50}$ value of 100 ng/mL in the monocyte activation assay (Table 4).

EXAMPLE 18

60% Ethanol Extraction at 60° C. and Direct 80% Alcohol Precipitation

One g of freeze-dried AFA was extracted at 60° C. with 60% ethanol, first with 7.5 mLs for 3 hours and then with 6.25 mLs for 12 hours. Supernatants from both extractions were combined (11.4 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 9.5% recovery of pre-ultrafiltrate NP16847 preparation and an $EC_{50}$ value of 100 ng/mL in the monocyte activation assay (Table 4). Removal of low molecular weight material (<100,000 daltons) resulted in 3.5% recovery of post-ultrafiltrate NP16847 preparation and an $EC_{50}$ value of about 75 ng/mL.

EXAMPLE 19

60% Ethanol Extraction at 70° C. and Direct 80% Alcohol Precipitation

One g of freeze-dried AFA was extracted at 70° C. with 60% ethanol, first with 7.5 mLs for 3 hours and then with 6.25 mLs for 12 hours. Supernatants from both extractions were combined (11.2 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 10.0% recovery of pre-ultrafiltrate NP16847 preparation and an $EC_{50}$ value of 50 ng/mL in the monocyte activation assay (Table 4).

EXAMPLE 20

60% Ethanol Extraction at 80° C. and Direct 80% Alcohol Precipitation

One g of freeze-dried AFA was extracted at 80° C. with 60% ethanol, first with 7.5 mLs for 3 hours and then with 6.25 mLs for 12 hours. Supernatants from both extractions were combined (11.2 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 11.2% recovery of pre-ultrafiltrate NP16847 preparation and an $EC_{50}$ value of 25 ng/mL in the monocyte activation assay (Table 4).

EXAMPLE 21

50% Ethanol Extraction at 23° C. and Direct 80% Alcohol Precipitation

One g of freeze-dried AFA was extracted at 23° C. with 50% ethanol, first with 7.5 mLs for 3 hours and then with 6.25 mLs for 12 hours. Supernatants from both extractions were combined (11.3 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 9.1% recovery of pre-ultrafiltrate NP16847 preparation and an $EC_{50}$ value of 200 ng/mL in the monocyte activation assay (Table 4).

EXAMPLE 22

50% Ethanol Extraction at 40° C. and Direct 80% Alcohol Precipitation

One g of freeze-dried AFA was extracted at 40° C. with 50% ethanol, first with 7.5 mLs for 3 hours and then with 6.25 mLs for 12 hours. Supernatants from both extractions were combined (11.3 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 8.9% recovery of pre-ultrafiltrate NP16847 preparation and an $EC_{50}$ value of 100 ng/mL in the monocyte activation assay (Table 4).

EXAMPLE 23

50% Ethanol Extraction at 50° C. and Direct 80% Alcohol Precipitation

One g of freeze-dried AFA was extracted at 50° C. with 50% ethanol, first with 7.5 mLs for 3 hours and then with 6.25 mLs for 12 hours. Supernatants from both extractions were combined (11.1 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 9.4% recovery of pre-ultrafiltrate NP16847 preparation and an $EC_{50}$ value of 75 ng/mL in the monocyte activation assay (Table 4).

EXAMPLE 24

50% Ethanol Extraction at 60° C. and Direct 80% Alcohol Precipitation

One g of freeze-dried AFA was extracted at 60° C. with 50% ethanol, first with 7.5 mLs for 3 hours and then with 6.25 mLs for 12 hours. Supernatants from both extractions were combined (11.4 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 10.8% recovery of pre-ultrafiltrate NP16847 preparation and an $EC_{50}$ value of 25 ng/mL in the monocyte activation assay (Table 4). Removal of low molecular weight material (<100,000 daltons) resulted in 4.5% recovery of post-ultrafiltrate NP16847 preparation and an $EC_{50}$ value of about 20 ng/mL.

EXAMPLE 25

50% Ethanol Extraction at 70° C. and Direct 80% Alcohol Precipitation

One g of freeze-dried AFA was extracted at 70° C. with 50% ethanol, first with 7.5 mLs for 3 hours and then with 6.25 mLs for 12 hours. Supernatants from both extractions were combined (11.4 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 10.2% recovery of pre-ultrafiltrate NP16847 preparation and an $EC_{50}$ value of 25 ng/mL in the monocyte activation assay (Table 4). Removal of low molecular weight material (<100,000 daltons) resulted in 5.6% recovery of post-ultrafiltrate NP16847 preparation and an $EC_{50}$ value of about 20 ng/mL.

EXAMPLE 26

50% Ethanol Extraction at 80° C. and Direct 80% Alcohol Precipitation

One g of freeze-dried AFA was extracted at 80° C. with 50% ethanol, first with 7.5 mLs for 3 hours and then with 6.25 mLs for 12 hours. Supernatants from both extractions were combined (11.2 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 11.7% recovery of pre-ultrafiltrate NP16847 preparation and an $EC_{50}$ value of 25 ng/mL in the monocyte activation assay (Table 4).

EXAMPLE 27

40% Ethanol Extraction at 23° C. and Direct 80% Alcohol Precipitation

One g of freeze-dried AFA was extracted at 23° C. with 40% ethanol, first with 7.5 mLs for 3 hours and then with 6.25 mLs for 12 hours. Supernatants from both extractions were combined (11.3 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 11.4% recovery of pre-ultrafiltrate NP16847 preparation and an $EC_{50}$ value of >250 ng/mL in the monocyte activation assay (Table 4).

EXAMPLE 28

40% Ethanol Extraction at 40° C. and Direct 80% Alcohol Precipitation

One g of freeze-dried AFA was extracted at 40° C. with 40% ethanol, first with 7.5 mLs for 3 hours and then with 6.25 mLs for 12 hours. Supernatants from both extractions were combined (11.4 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 10.7% recovery of pre-ultrafiltrate NP16847 preparation and an $EC_{50}$ value of 100 ng/mL in the monocyte activation assay (Table 4).

EXAMPLE 29

40% Ethanol Extraction at 50° C. and Direct 80% Alcohol Precipitation

One g of freeze-dried AFA was extracted at 50° C. with 40% ethanol, first with 7.5 mLs for 3 hours and then with 6.25 mLs for 12 hours. Supernatants from both extractions were combined (11.0 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 10.3% recovery of pre-ultrafiltrate NP16847 preparation and an $EC_{50}$ value of 100 ng/mL in the monocyte activation assay (Table 4).

EXAMPLE 30

40% Ethanol Extraction at 60° C. and Direct 80% Alcohol Precipitation

One g of freeze-dried AFA was extracted at 60° C. with 40% ethanol, first with 7.5 mLs for 3 hours and then with 6.25 mLs for 12 hours. Supernatants from both extractions were combined (11.4 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 10.8% recovery of pre-ultrafiltrate NP16847 preparation and an $EC_{50}$ value of 50 ng/mL in the monocyte activation assay (Table 4). Removal of low molecular weight material (<100,000 daltons) resulted in 3.3% recovery of post-ultrafiltrate NP16847 preparation and an $EC_{50}$ value of about 25 ng/mL.

EXAMPLE 31

40% Ethanol Extraction at 70° C. and Direct 80% Alcohol Precipitation

One g of freeze-dried AFA was extracted at 70° C. with 40% ethanol, first with 7.5 mLs for 3 hours and then with 6.25 mLs for 12 hours. Supernatants from both extractions were combined (11.4 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 11.1% recovery of pre-ultrafiltrate NP16847 preparation and an $EC_{50}$ value of 50 ng/mL in the monocyte activation assay (Table 4).

EXAMPLE 32

40% Ethanol Extraction at 80° C. and Direct 80% Alcohol Precipitation

One g of freeze-dried AFA was extracted at 80° C. with 40% ethanol, first with 7.5 mLs for 3 hours and then with 6.25 mLs for 12 hours. Supernatants from both extractions were combined (11.3 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 12.6% recovery of pre-ultrafiltrate NP16847 preparation and an $EC_{50}$, value of 50 ng/mL in the monocyte activation assay (Table 4). Removal of low molecular weight material (<100,000 daltons) resulted in 6.2% recovery of post-ultrafiltrate NP16847 preparation and an $EC_{50}$ value of about 30 ng/mL.

EXAMPLE 33

30% Ethanol Extraction at 23° C. and Direct 80% Alcohol Precipitation

One g of freeze-dried AFA was extracted at 23° C. with 30% ethanol, first with 7.5 mLs for 3 hours and then with 6.25 mLs for 12 hours. Supernatants from both extractions were combined (11.2 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 13.7% recovery of pre-ultrafiltrate NP16847 preparation and an $EC_{50}$ value of 200 ng/mL in the monocyte activation assay (Table 4).

EXAMPLE 34

30% Ethanol Extraction at 40° C. and Direct 80% Alcohol Precipitation

One g of freeze-dried AFA was extracted at 40° C. with 30% ethanol, first with 7.5 mLs for 3 hours and then with 6.25 mLs for 12 hours. Supernatants from both extractions were combined (11.3 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 13.8% recovery of pre-ultrafiltrate NP16847 preparation and an $EC_{50}$ value of 100 ng/mL in the monocyte activation assay (Table 4).

EXAMPLE 35

30% Ethanol Extraction at 50° C. and Direct 80% Alcohol Precipitation

One g of freeze-dried AFA was extracted at 50° C. with 30% ethanol, first with 7.5 mLs for 3 hours and then with 6.25 mLs for 12 hours. Supernatants from both extractions were combined (11.1 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 10.9% recovery of pre-ultrafiltrate NP16847 preparation and an $EC_{50}$ value of 100 ng/mL in the monocyte activation assay (Table 4).

EXAMPLE 36

30% Ethanol Extraction at 60° C. and Direct 80% Alcohol Precipitation

One g of freeze-dried AFA was extracted at 60° C. with 30% ethanol, first with 7.5 mLs for 3 hours and then with 6.25 mLs for 12 hours. Supernatants from both extractions were combined (11.2 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 10.5% recovery of pre-ultrafiltrate NP16847 preparation and an $EC_{50}$ value of 100 ng/mL in the monocyte activation assay (Table 4).

EXAMPLE 37

30% Ethanol Extraction at 70° C. and Direct 80% Alcohol Precipitation

One g of freeze-dried AFA was extracted at 70° C. with 30% ethanol, first with 7.5 mLs for 3 hours and then with 6.25 mLs for 12 hours. Supernatants from both extractions were combined (11.1 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 11.0% recovery of pre-ultrafiltrate NP16847 preparation and an $EC_{50}$ value of 75 ng/mL in the monocyte activation assay (Table 4).

EXAMPLE 38

30% Ethanol Extraction at 80° C. and Direct 80% Alcohol Precipitation

One g of freeze-dried AFA was extracted at 80° C. with 30% ethanol, first with 7.5 mLs for 3 hours and then with 6.25 mLs for 12 hours. Supernatants from both extractions were combined (11.0 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 11.9% recovery of pre-ultrafiltrate NP16847 preparation and an $EC_{50}$ value of 75 ng/mL in the monocyte activation assay (Table 4).

Table 4 summarizes the influence of both temperature and the ethanol concentration used during the initial extraction on the end-points described above. The endpoints used to evaluate the effectiveness of each extraction condition were percent recovery of the pre-ultrafiltrate in addition to its $EC_{50}$ value. The pre-ultrafiltrate material was selected for these analyses because of its potential use as either a dietary supplement or pharmaceutical preparation. Elimination of the ultrafiltration step would represent a substantial simplification of the isolation procedure.

The conditions used in Example 9 (70% ethanol/40° C.) resulted in 5.7% recovery of pre-ultrafiltrate NP16847 with an $EC_{50}$ value of 200 ng/mL. Increasing extraction temperatures above 40° C. coupled with the presence of 70% ethanol during the initial extraction improved recovery and specific activity of the NP16847 polysaccharide preparation. However, decreasing the extraction temperature from 40° C. to 23° C. with 70% ethanol, or any other concentration of ethanol, did not result in lower $EC_{50}$ values. At this temperature (23° C.), recoveries were enhanced at lower ethanol concentrations. Part of this increased recovery was probably due to a more efficient extraction of phycocyanin as evidenced by the enhanced blue color of the material. Extraction at higher temperatures using 70% ethanol slightly enhanced recovery and substantially increased specific activity (e.g. 70% ethanol/80° C.). Extraction with 50% ethanol at any temperature above 40° C. resulted in lower $EC_{50}$ values as compared with other ethanol concentrations. At ethanol concentrations above and below 50% ethanol, specific activities generally decreased at each temperature condition. Ethanol concentrations above and below 50% had opposite effects on recovery: recoveries decreased with higher ethanol concentration but slightly increased with lower concentrations (at temperatures of 50° C. and below). The lower recoveries coupled with decreased specific activity at ethanol concentrations higher than 50% suggest that less NP16847 is being extracted under these conditions. For ethanol concentrations below 50%, the higher recoveries coupled with decreased specific activity suggest that more inactive material is extracted along with NP16847. At temperatures below 60° C. with 30% and 40% ethanol, part of this inactive material is most likely due to more effective extraction of phycocyanin, again evidenced by the enhanced blue color of the precipitate.

The region of Table 4 from 60° C.–80° C. at 50% ethanol represented conditions for both optimal recovery and specific activity. The preferred temperature range is between 60° C. and 70° C. (Examples 24 and 25) because further analysis of both the pre- and post-ultrafiltrate material derived from the 80° C., 40% to 60% ethanol extraction conditions showed substantial amounts of water insoluble material. These optimal conditions yield post-ultrafiltrate recoveries between 4.5% and 5.6% (7.5 to 9.3 times more than the earlier 70% ethanol/40° C. condition from Example 1) and an $EC_{50}$ value of about 20 ng/mL (5 times less than the 70% ethanol/40° C. condition).

EXAMPLE 39

Shorter Extraction Times

The data in Table 4 were collected on material extracted twice, first for 3 hours and second for 12 hours, under each condition. To optimize for large scale extraction of NP16847, shorter extractions times of 1 hour each were tested and found to be equivalent in terms of both recovery and specific activity.

EXAMPLE 40

Single Hot Water Extraction at 95° C. for 30 Minutes

Prior art procedures for the isolation of immunostimulatory polysaccharides from other types of microalgae (17, 27) typically involve a single hot water extraction at 95° C. for 30 minutes. To evaluate this method, 1 g of freeze-dried AFA was extracted once with 20 mLs of water at 95° C. for 30 minutes. The water extract was adjusted to 80% ethanol and incubated at −20° C. for several hours. The precipitate collected represented a recovery of 12.1% but contained very little NP16847 since the $EC_{50}$ of this material was about 500 ng/mL. Ultrafiltration resulted in a recovery of 5.1% and no change in specific activity. Clearly these conditions are not suitable for extraction of NP16847 from AFA.

EXAMPLE 41

Water Extraction at 4° C. Followed by Re-Extraction with 50% Ethanol/60° C.

It is possible that contaminating polar material can be selectively removed by an initial water extraction without substantial loss of NP16847. A two stage extraction procedure was tested to evaluate this approach. The first stage involved an initial water extraction of AFA at 4° C. followed by a second stage re-extraction of AFA at optimal conditions (50% ethanol/60° C.). Although the specific activity of NP16847 using this method was comparable to the optimal conditions alone, the recovery was about 70% less for both pre- and post-ultrafiltrate.

EXAMPLE 42

Water Extraction at 23° C. Followed by Re-Extraction with 50% Ethanol/60° C.

The procedure used in Example 41 was slightly modified by increasing the extraction temperature from 4° C. to 23° C. Thus, the first extraction involved an initial water extraction of AFA at 23° C. followed by a second stage re-extraction of AFA at optimal conditions (50% ethanol/60° C.). The results were similar to those in Example 41 (i.e. the specific activity was comparable to optimal conditions, yet the recovery was about 70% less for both pre- and post-ultrafiltrate).

EXAMPLE 43

Water Extraction at 40° C. Followed by Re-Extraction with 50% Ethanol/60° C.

The procedure used in Example 41 was slightly modified by increasing the extraction temperature from 4° C. to 40° C. Thus, the first extraction involved an initial water extraction of AFA at 40° C. followed by a second stage re-extraction of AFA at optimal conditions (50% ethanol/60° C.). The results were similar to those in Example 41 (i.e. the specific activity was comparable to optimal conditions, yet the recovery was about 70% less for both pre- and post-ultrafiltrate).

EXAMPLE 44

Extraction with 70% Ethanol/40° C. Followed by Re-Extraction with 50% Ethanol/60° C.

It is possible that contaminating non-polar material can be selectively removed by an initial ethanol extraction without substantial loss of NP16847. To evaluate this approach a two stage extraction procedure was tested. The first stage involved an initial extraction of AFA with 70% ethanol at 40° C. followed by a second stage re-extraction of AFA at optimal conditions (50% ethanol/60° C.). Although this procedure gave a slightly better $EC_{50}$ value (10 ng/mL) than did Examples 24 and 25 for the post-ultrafiltrate NP16847, the recovery was only 1.0%. The pre-ultrafiltrate had a recovery of 2.2% with an $EC_{50}$ value of 20 ng/mL.

One property of purified NP16847 was that it appeared to adhere to polypropylene pipette tips. To avoid exaggerated $EC_{50}$ values caused by carryover of the material during serial dilutions, pipette tips were changed between each dilution.

Chromatographic analysis of NP16847 before and after ultrafiltration is displayed in FIGS. 5–11. NP16847 preparation isolated using the procedure outlined in Example 1 generally eluted as a broad single peak (FIG. 1). However, using the modified procedures (Examples 4–9), post-ultrafiltrate NP16847 eluted as a broad region containing what appears to be three peaks (refer to FIGS. 5–10). This triple peak characteristic can however be changed into a broad single peak by solvent partitioning of these post-ultrafiltrate NP16847 preparations between water:chloroform (1:1). FIGS. 9 and 10 display the shape of the purified NP16847 polysaccharide peak after this partitioning with chloroform. The large peak to the far right of each chromatogram also occurs in the blank control and is therefore due to chloroform. There are several possible explanations for the transformation of the complex peak into a single peak. It is possible that there is a trace amount of non-polar or fat-like material associated with NP16847 that is responsible for inter-molecular association of the NP16847 polysaccharides. These larger complexes would give rise to the multiple peaks. Removal of the non-polar material with chloroform would break these associations and give rise to the single chromatographic peak. The possible association of a fat-like or non-polar material with NP16847 might explain why this polysaccharide material is extractable using high concentrations of aqueous ethanol. Whether NP16847 is a single polysaccharide or a mixture of related polysaccharides is difficult to evaluate due to the very high molecular weight of this material. The multiple peak phenomenon does not occur however in the pre- and post-ultrafiltrate NP16847 preparations obtained using optimal extraction conditions (50% ethanol/60° C.–70° C., refer to FIG. 11). This may be due to either lower ethanol concentration or higher extraction temperatures or a combination of these two factors.

Carbohydrate composition of different NP16847 preparations was evaluated using GC-mass spectrometry analysis of TMS-methyl glycosides (Table 5). NP16847 material from Example 1 (NP1) was re-analyzed and found to have an identical carbohydrate composition profile as previously determined. Since a different batch of AFA (purchased from another company) was used in Examples 4–44 a preparation of NP16847 was isolated from this new material using the extraction procedure of Example 1 (NP2). Both this NP16847 preparation and NP1 have a comparable glycosyl composition, indicating consistency between different batches of AFA. The NP2 preparation however, was five times less active than NP1 (Table 5) due to partial loss of active polysaccharides into the n-butanol phase during the n-butanol/water partitioning. In general, similar carbohydrate compositions were also found in pre- and post-ultrafiltrate NP16847 preparations (NP3–NP6) obtained using optimal extraction conditions (50% ethanol at 60° C. and 70° C.). Pre-ultrafiltrate NP16847 was, however, consistently higher in glucose composition and lower In N-acetylated sugar units than post-ultrafiltrate preparations. Based on the consistency of carbohydrate composition between these different NP16847 preparations (NP1–NP7), it is clear that the major glycosyl residues present in this material are mannose, rhamnose, arabinose and glucose. In order to identify the O-methylated sugars detected during the TMS-methyl glycoside procedure, glycosyl composition was also determined using alditol acetate analysis. Methylated sugar residues contained in these preparations include 2-methyl rhamnose, 3-methyl rhamnose, 4-methyl rhamnose, 2-methyl fucose, 3-methyl arabinose and 3-methyl mannose. Interestingly, these NP16847 preparations contain 5.1–12.5% methylated carbohydrate residues and a high percent of deoxyhexoses (e.g. rhamnose and fucose). Both these characteristics may explain the unusual extractability of NP16847 polysaccharide material using relatively high concentrations of aqueous ethanol.

Because the samples tested (NP1–NP7) represent up to a ~50-fold difference in $EC_{50}$ values, one would expect to see some difference in carbohydrate composition among them. Since this is not the case, it is obvious that the purity or activity of NP16847 preparations cannot be determined using this parameter. Therefore, NP16847 preparations would more appropriately be characterized by biological activity, size and extractability in aqueous ethanol. It may be that a unique structural feature is responsible for NP16847's ability to activate monocytes/macrophages rather than a specific carbohydrate composition. It is also possible that the carbohydrate composition of NP1–NP7 reflects polysaccharides extractable with aqueous ethanol solutions and immunostimulatory ones would be present as a structural class within this group. This interpretation is supported by the observation that material obtained with hot water extraction (NP8 and NP9) has a very different carbohydrate profile than NP16847 preparations isolated using aqueous ethanol extraction (NP1–NP7). The predominant glycosyl residue from both pre- and post-ultrafiltrate material obtained from hot water extraction of AFA was glucose (Table 5). Another distinguishing characteristic of NP8 and NP9 is the lower percent composition of rhamnose as compared with NP16847 material isolated using aqueous ethanol extraction.

EXAMPLE 45

Extraction with 60% Methanol at 65° C. and Direct 80% Alcohol Precipitation

One g of freeze-dried AFA was extracted at 65° C. with 60% methanol, first with 7.5 mLs for 1 hour and then with 6.25 mLs for 1 hour. Supernatants from both extractions were combined (11.5 mLs) following centrifugation. The methanol concentration of the supernatant was adjusted to 80% by the addition of cold 100% methanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 1.8% recovery of pre-ultrafiltrate NP16847 preparation and an $EC_{50}$ value of 75 ng/mL in the monocyte activation assay.

EXAMPLE 46

Extraction with 40% Isopropanol at 65° C. and Direct 80% Alcohol Precipitation

One g of freeze-dried AFA was extracted at 65° C. with 40% isopropanol, first with 7.5 mLs for 1 hour and then with 6.25 mLs for 1 hour. Supernatants from both extractions were combined (11.5 mLs) following centrifugation. The isopropanol concentration of the supernatant was adjusted to 80% by the addition of cold 100% isopropanol. Following incubation at −20° C. for several hours, precipitates were collected by centrifugation and subsequently washed with cold 95% ethanol. The isolated material was dried under vacuum and dissolved in water at 10 mg/mL. This extraction procedure resulted in 12.0% recovery of pre-ultrafiltrate NP16847 preparation and an $EC_{50}$ value of 100 ng/mL in the monocyte activation assay.

EXAMPLE 47

Extraction with 100% Ethanol by Reflux and Precipitation by Cooling to −20° C.

One g of freeze-dried AFA was extracted by reflux using 100% ethanol, first with 8.0 mLs for 1 hour and then with 6.50 mLs for 1 hour. Supernatants from both extractions were combined (11.0 mLs) following centrifugation. Combined supernatant was then stored at −20° C. for several hours and perceptible material removed by centrifugation. Precipitate was subsequently washed with washed with cold 95% ethanol. The isolated material was dried under vacuum and dissolved in water at 10 mg/mL. This extraction procedure resulted in 0.68% recovery of pre-ultrafiltrate NP16847 preparation and an $EC_{50}$ value of about 750 ng/mL in the monocyte activation assay.

EXAMPLE 48

Extraction of Immunostimulatory Polysaccharide Material Using Aqueous Alcohol from Other Food-Grade Microalgae (*Chlorella* and *Spirulina*)

The process of obtaining NP16847 from AFA using an initial extraction with aqueous alcohol, under optimal conditions, results in a preparation that is 20 times more active than material obtained using a hot water extraction ($EC_{50}$ values for monocyte activation of 25 ng/mL verses 500 ng/mL, respectively).

The same aqueous alcohol extraction procedure can also be applied to other food-grade microalgae to obtain preparations that are enriched for immunostimulatory polysaccharides. For example, previous patents (16, 17, 27) have reported that *Chlorella* species and *Spirulina* species contain immunostimulatory polysaccharides that are extracted using hot water. However, extraction with aqueous alcohol (instead of hot water) results in selective enrichment for polysaccharides that are immunostimulatory and thereby results in preparations from these organisms that exhibit superior biological activity as well as a higher percent recovery of active material (see experiments below).

The following food-grade microalgae were used in these experiments: *Chlorella pyrenoidosa* (Sun *Chlorella*, Lot. No. WS 1422) and *Spirulina platensis* (Nature's Way, Lot. No. 912091). All polysaccharide preparations represent pre-ultrafiltrate material. For preparation of hot water extracts, 1 g of freeze-dried microalgae was extracted once with 20 mLs of water at 95° C. for 30 minutes. Hot water extracts were adjusted to 80% ethanol and incubated at −20° C. overnight. The precipitate collected from *Chlorella* represented a recovery of 13.2% and an $EC_{50}$ value of 1,000 ng/mL. The precipitate collected from *Spirulina* represented a recovery of 16.5% and an $EC_{50}$ value of 10,000 ng/mL for monocyte/macrophage activation.

Aqueous ethanol extracts were prepared by systematically changing both temperature and solvent concentration (percent ethanol in water) used during the initial extraction. The endpoints of percent recovery and $EC_{50}$ value for macrophage activation were used to determine optimal conditions for preparation of immunostimulatory polysaccharide material. *Chlorella* and *Spirulina* extracts were prepared using the following procedure. One g of freeze-dried microalgae was extracted at the appropriate temperature, first with 7.5 mLs of aqueous ethanol solvent for 2 hours and then with 6.25 mLs of aqueous ethanol solvent for 2 hours. Supernatants from both extractions were combined (11.3 mLs) following centrifugation. The ethanol concentration of the supernatant was adjusted to 80% by the addition of cold 100% ethanol. Following incubation at −20° C. for several hours, precipitates were collected by centrifugation and subsequently washed with cold 95% ethanol. The isolated material was dried under vacuum and dissolved in water at 10 mg/mL.

The extraction conditions for both optimal recovery and specific activity of immunostimulatory polysaccharide preparations from *Chlorella* and *Spirulina* were similar to the optimal conditions (60° C.–70° C. at 50% ethanol) for extraction of NP16847 from AFA. For *Chlorella*, optimal conditions for preparation of immunostimulatory polysaccharide material involve an initial extraction with 50% ethanol at 70° C. This condition yields a pre-ultrafiltrate recovery of 6.5% with an $EC_{50}$ value of 25 ng/mL. For *Spirulina*, optimal conditions for preparation of immunostimulatory polysaccharide material involve an initial extraction with 40%–50% ethanol at temperatures between 50° C. and 70° C. These conditions yield pre-ultrafiltrate recoveries of about 9.0% with $EC_{50}$ values of 500 ng/mL. By comparison, although hot water extracts result in recoveries of about 2 times more material, they are 20 to 40 times less active than the preparations obtained using optimal extraction conditions with aqueous ethanol.

In summary, a simple and effective isolation procedure for optimal recovery of NP16847 from AFA was developed. The optimal extraction method for the pre-ultrafiltrate NP16847 preparation is a direct alcohol precipitation (80% at −20° C.) from two pooled extracts of 1 hour each using 50% ethanol at 60° C.-70° C. This pre-ultrafiltrate NP16847 preparation represents 11% recovery of AFA dry weight. Using one additional step involving ultrafiltration to exclude all material below 100,000 daltons, a relatively pure preparation of NP16847 polysaccharides can be obtained with recoveries between 4.5% and 5.6%. Both pre- and post-ultrafiltrate preparations have approximately the same $EC_{50}$ value (25 ng/mL for pre-ultrafiltrate and 20 ng/mL for post-ultrafiltrate). In comparison with the NP16847 material obtained in Example 1 (70% ethanol extraction at 40° C.), this optimized post-ultrafiltrate preparation contains between 7.5 and 9.3 times more NP16847 with 5 times greater activity. This procedure is well suited for both a preparation of a dietary supplement (botanical) extract as well as a bulk pharmaceutical product.

The same process described for obtaining immunostimulatory polysaccharide compositions (NP16847) from AFA microalgae can be used to obtain preparations from other microalgae (which include *Chlorella* species and *Spirulina* species) that are enriched for immunostimulatory polysaccharides (for example that activate monocytes/macrophages). The unique carbohydrate composition of all three microalgae polysaccharide preparations allows the use of a procedure that selectively enriches for those that are immunostimulatory. These polysaccharides are extracted very poorly using the traditional hot water extraction procedure. Hot water preparations are 20 to 40 times less active than those using the optimized procedure.

Pharmaceutical Formulations

The present invention further includes low cost bulk polysaccharide preparations. The microalgae from which these polysaccharide preparations are isolated can be grown in tanks similar to current commercial methods that cultivate these microalgae for human consumption. This means that there would not be a supply problem, which is often a major issue for drug development of compounds isolated from natural products. The instant polysaccharide preparations exist in high concentrations (between 6.5% and 11% of microalgae dry weight) and can be isolated using the simple, fast and low-cost techniques of the present invention.

Since the present polysaccharide preparations are useful as agents for immunotherapy in the treatment of immunodeficiency disorders, cancer, wound healing and infectious diseases, the present invention includes pharmaceutical compositions containing the instant polysaccharide preparations optionally in combination with acceptable pharmaceutical carriers or excipients.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

The amount of composition administered will be dependent upon the condition being treated, the subject being treated, on the subject's weight, the severity of the affliction, the manner of administration and the judgment of the personalizing physician.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the compositions compounds into preparation which can be used pharmaceutically. Proper formulation is dependent upon the route of administration chosen.

For injection, the agents of the invention may be formulated in aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compositions can be formulated readily by combining the active compositions with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as fit, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a power mix of the compound and a suitable powder base such as lactose or starch.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active composition may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compositions may also be formulated in rectal compositions such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable routes of administration may, for example, include oral, rectal, transmucosal, transdermal, or intestinal administration, parenteral delivery, including intramuscular, subcutaneous, intramedullary injections, as well as intrathecal, direct intraventricular, intravenous, intraperitoneal, intranasal, or intraocular injections.

Alternatively, one may administer the composition in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a composition of the invention formulated in a compatible pharmaceutical carrier may also be prepared, placed in an appropriate container, and labeled for treatment of an indicated condition. Suitable conditions indicated on the label may include treatment of a disease.

Dietary Supplements

Dietary supplements suitable for use in the present invention include compositions wherein the active ingredients are contained in an effective amount to achieve its intended purpose. More specifically, an effective amount means an amount effective to prevent development of or to alleviate the existing symptoms of the subject being treated. Determination of the effective amounts is well within the capability of those skilled in the art, especially in light of the detailed disclosure provided herein. The amount of composition administered will be dependent upon the condition being treated, the subject being treated, on the subjects weight, the severity of the affliction, the manner of administration and the judgment of the personalizing physician.

The ingredients of the dietary supplement of this invention are contained in acceptable excipients and/or carriers for oral consumption. The actual form of the carrier, and thus, the dietary supplement itself, may not be critical. The carrier may be a liquid, gel, gelcap, capsule, powder, solid tablet (coated or non-coated), tea or the like. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, agar, lactose, methylcellulose, povidone, carboxymethylcellulose, corn starch, and the like (including mixtures thereof). The various ingredients and the excipient and/or carrier are mixed and formed, into the desired form using conventional techniques. Dose levels/unit can be adjusted to provide the recommended levels of ingredients per day in a reasonable number of units.

The dietary supplement may also contain optional ingredients including, for example, herbs, vitamins, minerals, enhancers, colorants, sweeteners, flavorants, inert ingredients, and the like. Such optional ingredients may be either naturally occurring or concentrated forms. Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults.

REFERENCES

All references or citations made or referred to in this Application are expressly incorporated into the specification by reference thereto.

1. Hadden, J. W. Immunostimulants. *Immunol. Today* 1993, 14, 275–280.
2. Masihi, K. N. Immunomodulatory agents for prophylaxis and therapy of infections. *Int. J. Antimicrob. Agents* 2000, 14, 181–191.
3. Van Kampen, K. R. Immunotherapy and cytokines. *Semin. Vet. Med. Surg. (Small Anim.)* 1997, 12, 186–192.
4. Franz, G. Polysaccharides in pharmacy. Current applications and future concepts. *Planta Med.* 1989, 55, 493–497.
5. Frank, M. O.; Mandell, G. L. Immunomodulators. In *Principles and Practice of Infectious Diseases, chapter 33, 4th ed.*; Mandell, G. L., Bennett, J. E., Dolin, R., Eds.; Churchill Livingstone: New York, 1995; pp 450–458.
6. Wilson, K. Wound healing: the role of macrophages. *Nurs. Crit. Care* 1997, 2, 291–296.
7. King, G. K.; Yates, K. M.; Greenlee, P. G.; Pierce, K. R.; Ford, C. R.; McAnalley, B. H.; Tizard, I. R. The effect of Acemannan Immunostimulant in combination with surgery and radiation therapy on spontaneous canine and feline fibrosarcomas. *J. Am. Animal Hosp. Assoc.* 1995, 31:439–47.
8. Natori, T.; Motoki, K.; Higa, T.; Koezuka, Y. KRN7000 as a new type of antitumor and immunostimulatory drug. In *Drugs from the Sea*; Fusetani, N., Ed.; Karger: New York, 2000; pp 86–97.
9. Shu, Y. Z. Recent natural products based drug development: A pharmaceutical industry perspective. *J. Nat. Prod.* 1998, 61, 1053–1071.
10. Ciferri, O. *Spirulina*, the edible microorganism. *Microbiol. Rev.* 1983, 47, 551–578.
11. Dantas, D. C.; Kaneno, R.; Queiroz, M. L. The effects of *Chlorella vulgaris* in the protection of mice infected with *Listeria monocytogenes*. Role of natural killer cells. *Immunopharmacol. Immunotoxicol.* 1999, 21, 609–619.
12. Dantas, D.C.; Queiroz, M. L. Effects of *Chlorella vulgaris* on bone marrow progenitor cells of mice infected with *Listeria monocytogenes*. *Int. J. Immunopharmacol.* 1999, 21, 499–508.
13. Qureshi, M. A.; Garlich, J. D.; Kidd, M. T. Dietary *Spirulina platensis* enhances humoral and cell-mediated immune functions in chickens. *Immunopharmacol. Immunotoxicol.* 1996, 18, 465–476.
14. Mathew, B.; Sankaranarayanan, R.; Nair, P. P.; Varghese, C.; Somanathan, T.; Amma, B. P.; Amma, N. S.; Nair, M. K. Evaluation of chemoprevention of oral cancer with *Spirulina fusiformis*. *Nutr. Cancer* 1995, 24, 197–202.
15. Jensen, G. S.; Ginsberg, D. I.; Huerta, P.; Citton, M.; Drapeau, C. Consumption of *Aphanizomenon flos-aquae* has rapid effects on the circulation and function of immune cells in humans. *JANA* 2000, 2, 50–58.
16. Umezawa, I.; Komiyama, K. Acidic polysaccharide CH-1 isolated from *Chlorella pyrenoidosa* and the use thereof. U.S. Pat. No. 4,533,548, 1985.
17. Watanabe, S.; Seto, A. Ingredient effective for activating immunity obtained from *Chlorella minutissima*. U.S. Pat. No. 4,831,020, 1989.
18. Watanabe, S.; Fujita, T. Immunopotentiating agent having anti-tumor activity U.S. Pat. No. 4,786,496, 1988.
19. Shinpo, K. Anticancer agent. U.S. Pat. No. 4,822,612, 1989.
20. Noda, K.; Ohno, N.; Tanaka, K.; Okuda, M.; Yadomae, T.; Nomoto, K.; Shoyama, Y. A new type of biological response modifier from *Chlorella vulgaris* which needs protein moiety to show an antitumor activity. *Phytother. Res.* 1998, 12, 309–319.
21. Tanaka, T.; Yamada, A.; Noda, K.; Hasegawa, T.; Okuda, M.; Shoyama, Y.; Nomoto, K. A novel glycoprotein obtained from *Chlorella vulgaris* strain CK22 shows antimetastatic immunopotentiation. *Cancer Immunol. Immunother.* 1998, 45, 313–320.
22. Noda, K.; Ohno, N.; Tanaka, K.; Kamiya, N.; Okuda, M.; Yadomae, T.; Nomoto, K.; Shoyama, Y. A water-soluble antitumor glycoprotein from *Chlorella vulgaris*. *Planta Med.* 1996, 62, 423–426.

23. Matsueda, S.; Shinpo, K.; Tanaka, K.; Abe, K.; Karasawa, H. Studies on anti-tumor active glycoprotein from *Chlorella vulgaris*. II. *Sci. Rep. Hirosaki Univ.* 1983, 30, 127–131.

24. Morimoto, A.; Nagatsu, A.; Murakami, N.; Sakakibara, J.; Tokuda, H.; Nishino, H.; Iwashima, A. Anti-tumor-promoting glyceroglycolipids from the green alga, *Chlorella vulgaris*. *Phytochemistry* 1995, 40, 1433–1437.

25. Mishima, T.; Murata, J.; Toyoshima, M.; Fujii, H.; Nakajima, M.; Hayashi, T.; Kato, T.; Saiki, I. Inhibition of tumor invasion and metastasis by calcium spirulan (Ca-SP), a novel sulfated polysaccharide derived from a blue-green alga, *Spirulina platensis*. *Clin. Exp. Metastasis* 1998, 16, 541–550.

26. Lee, J. B.; Hayashi, T.; Hayashi, K.; Sankawa, U.; Maeda, M.; Nemoto, T.; Nakanishi, H. Further purification and structural analysis of calcium spirulan from *Spirulina platensis*. *J. Nat. Prod.* 1998, 61, 1101–1104.

27. Hayashi, T.; Hayashi, K.; Kojima, I. Antiviral polysaccharide. U.S. Pat. No. 5,585,365, 1996.

28. Wang, H.; Zeng, H. P.; Yang, S. Z. Isolation, purification and some properties of the water-soluble polysaccharides from *Spirulina platensis*. *Jingxi Huagong* 1999, 16, 26–29.

29. Wu, J.; Zhang, C.; Liu, Y. Isolation, purification and immunological activities of extracellular polysaccharide EP II from *Spirulina maxima*. *Yaowu Shengwu Jishu* 1999, 6, 99–102.

30. Zhang, Y.; Li, H.; Gao, J.; Shen, Z.; Lin, W.; Fu, H. New process for separation and purification of polysaccharides from *Spirulina platensis*. *Shipin Yu Fajiao Gongye* 1999, 25, 15–18.

31. Elgert, K. D.; Alleva, D. G.; Mullins, D. W. Tumor-induced immune dysfunction: the macrophage connection. *J. Leukoc. Biol.* 1998, 64, 275–290.

32. Morrissette, N.; Gold, E.; Aderem, A. The macrophage: a cell for all seasons. *Trends Cell. Biol.* 1999, 9, 199–201.

33. Gordon, S. The role of the macrophage in immune regulation. *Res. Immunol.* 1998, 149, 685–688.

34. Adams, D. O.; Hamilton, T. A. Molecular basis of macrophage activation: diversity and its origins. In *The Natural Immune System: The Macrophage*; Lewis, C. E., McGee, J. O'D., Eds.; Oxford University Press Inc.: New York, 1992; pp 75–114.

35. May, M. J.; Ghosh, S. Signal transduction through NF-kappa B. *Immunol. Today* 1998, 19, 80–88.

36. Baeuerle, P. A.; Henkel, T. Function and activation of NF-kappa B in the immune system. *Annu. Rev. Immunol.* 1994, 12, 141–179.

37. Chang, C. C.; Zhang, J.; Lombardi, L.; Neri, A.; Dalla-Favera, R. Mechanism of expression and role in transcriptional control of the proto-oncogene NFKB-2/LYT-10. *Oncogene*, 1994, 9, 923–933.

38. York, W. S.; Darvill, A. G.; McNeil, M.; Stevenson, T. T.; Albersheim, P. Isolation and characterization of plant cell walls and cell wall components. *Methods Enzymol.* 1986, 118, 3–40.

39. Hakomori, S. Rapid permethylation of glycolipids and polysaccharides, catalyzed by methylsulfinyl carbanion in dimethyl sulfoxide. *J. Biochem. Tokyo* 1964, 55, 205–208.

40. Azadi, P.; O'Neill, M. A.; Bergmann, C.; Darvill, A. G.; Albersheim, P. The backbone of the pectic polysaccharide rhamnogalacturonan I is cleaved by an endohydrolase and an endolyase. *Glycobiology* 1995, 5, 783–789.

41. Sturgeon, R. J. Monosaccharides: colorimetric assays. In *Methods in Plant Biochemistry, vol. 2, chapter 1*; Dey, P. M., Harborne, J. B., Eds.; Academic Press: New York, 1990; pp 4–12.

42. Su, S.; Vivier, R. G.; Dickson, M. C.; Thomas, N.; Kendrick, M. K.; Williamson, N. M.; Anson, J. G.; Houston, J. G.; Craig, F. F. High-throughput RT-PCR analysis of multiple transcripts using a microplate RNA isolation procedure. *Biotechniques*, 1997, 22, 1107–1113.

43. Zhang, X.; Liu, M.; Liu, Q.; Wan, H.; Shanghao, L. Preliminary isolation and spectral characteristics of phycocyanin of *Gymnodinium cyaneum*. *Kexue Tongbao* 1982, 27, 115–117.

44. Ogawa, K.; Tezuka, S.; Tsucha, Y.; Tanabe, Y.; Iwamoto, H. Phycocyanin as a chewing gum coloring agent. Japanese Patent 54138156, 1979.

TABLE 1

Glycosyl composition and linkage analysis for isolated polysaccharide preparation NP16847 from AFA microalgae obtained using extraction procedure in Example 1. Data obtained from one experiment.

| Glycosyl Residue | Mole % | Glycosyl Linkage | 0% total area |
|---|---|---|---|
| Mannose | 16.0 | 2-Mannose/3-Mannose | 13.4 |
| Glucose | 13.1 | 4-Rhamnose/T-Mannose | 10.6 |
| 4-Me-Mannose | 11.2 | 2-Rhamnose | 7.6 |
| Rhamnose | 10.3 | T-Rhamnose | 7.5 |
| 2-Me-Rhamnose | 8.1 | 3-Rhamnose | 6.9 |
| Galactose | 8.0 | 2-Glucose | 5.3 |
| Fucose | 7.0 | 2-Galactose | 4.8 |
| N-Acetyl Galactosamine | 7.0 | 2-Fucose | 4.7 |
| N-Acetyl Glucosamine | 5.8 | 3,4-Fucose | 4.5 |
| Xylose | 4.8 | 4-Glucose | 4.4 |
| 2-Me-Fucose | 3.1 | 3-Xylose | 4.4 |
| 3-Me-Galactose | 2.6 | 4-Fucose/T-Galactose | 4.3 |
| 3-Me-Arabinose | 1.8 | T-Xylose | 3.2 |
| Arabinose | 1.6 | unidentified | 2.7 |
| 2,3-diMe-Arabinose | 1.2 | T-Fucose | 2.5 |
| | | 4-Mannose | 2.2 |
| | | 2-Arabinose (pyranose) | 2.1 |
| | | 4-Galactose | 2.1 |
| | | 2,3,6-Galactose | 2.1 |
| | | 3-Galactose | 1.4 |
| | | 3,5-Arabinose(f)/3,4-Arabinose(p) | 1.3 |
| | | 2,6-Glucose | 1.2 |
| | | 6-Mannose | 0.6 |

Note: Methyl groups are represented by "Me". All glycosyl linkages are also 1-linked unless otherwise specified. Glycosyl abbreviations represent the following: "T" for terminal linkage, "f" for furanose, and "p" for pyranose. Presence of two glycosyl units indicates co-elution of components during analysis.

TABLE 2

Glycosyl composition and linkage analysis for isolated polysaccharide preparation NP16848 from *Chlorella pyrenoidosa* microalgae obtained using extraction procedure in Example 2. Data obtained from one experiment.

| Glycosyl Residue | Mole % | Glycosyl Linkage | % total area |
|---|---|---|---|
| Arabinose | 31.6 | T-Galactose (furanose) | 12.2 |
| Galactose | 26.8 | 2-Glucose | 9.2 |
| Rhamnose | 12.4 | 6-Galactose (pyranose) | 8.6 |
| Glucose | 5.4 | 2,3-Rhamnose | 8.4 |
| 3-Me-Arabinose | 3.0 | T-Glucose | 5.9 |
| 3-Me-Mannose | 2.5 | T-Arabinose (furanose) | 5.5 |
| Xylose | 2.4 | 2-Arabinose (furanose) | 5.4 |

TABLE 2-continued

Glycosyl composition and linkage analysis for isolated polysaccharide preparation NP16848 from *Chlorella pyrenoidosa* microalgae obtained using extraction procedure in Example 2. Data obtained from one experiment.

| Glycosyl Residue | Mole % | Glycosyl Linkage | % total area |
| --- | --- | --- | --- |
| 4-Me-Arabinose | 2.4 | 3,6-Galactose | 5.1 |
| Mannose | 2.3 | 2,3,6-Galactose | 4.9 |
| Ribose | 1.9 | T-Mannose/3-Rha/4-Rha | 3.7 |
| 2,4-diMe-Arabinose | 1.3 | 2,3-Arabinose (furanose) | 3.3 |
| 3-Me-Galactose | 1.2 | T-Arabinose (pyranose) | 2.8 |
| 3-Me-Xylose | 0.9 | 6-Galactose (furanose) | 2.6 |
| 3-Me-Rhamnose | 0.9 | 3-Hexose (furanose) | 2.4 |
| 3,5-diMe-hexose | 0.9 | 3-Galactose | 2.3 |
| 6-Me-Galactose | 0.7 | 2-pento (furanose) | 2.1 |
| Glycerol | 0.5 | 4-Glucose/2,4-Ara(p)/2,5-Ara(f) | 2.1 |
| 2-keto-3-deoxy-Octulosonic acid | 0.5 | T-Xylose (pyranose) | 1.8 |
| 2,3,6-triMe-Mannose | 0.4 | 4,6-Galactose | 1.9 |
| 3,6-diMe-Mannose | 0.4 | 4-Galactose | 1.9 |
| 2,3-diMe-Mannose | 0.4 | 3,4-Galactose | 1.7 |
| 2-Me-Galactose | 0.4 | T-Galactose (pyranose) | 1.4 |
| N-Acetyl Galactosamine | 0.3 | 3-pentose (furanose) | 1.3 |
| N-Acetyl Glucosamine | 0.3 | 3,4-Rhamnose | 1.1 |
| amino sugar | 0.3 | 2-Mannose/3-Mannose | 1.1 |
|  |  | 3-Arabinose (furanose) | 1.0 |
|  |  | 2,6-Glucose | 0.5 |

Note: Methyl groups are represented by "Me". All glycosyl linkages are also 1-linked unless otherwise specified. Glycosyl abbreviations represent the following: "Rha" for rhamnose, "Ara" for arabinose, "T" for terminal linkage, "f" for furanose, and "p" for pyranose. Presence of two or three glycosyl units indicates co-elution of components during analysis.

TABLE 3

Glycosyl composition and linkage analysis for isolated polysaccharide preparation NP16846 from *Spirulina platensis* microalgae obtained using extraction procedure in Example 3. Data obtained from one experiment.

| Glycosyl Residue | Mole % | Glycosyl Linkage | % total area |
| --- | --- | --- | --- |
| Rhamnose | 35.4 | 3-Rhamnose/T-Glucuronic Acid | 25.8 |
| Glucuronic acid | 9.7 | 4-Galactose | 7.8 |
| Fucose | 7.7 | 4-Glucuronic acid | 7.3 |
| Galactose | 7.1 | 3,4-Glucuronic acid | 6.9 |
| 2-Me-Rhamnose | 5.9 | 2-Rhamnose | 5.7 |
| Xylose | 5.5 | 3-Fucose | 5.1 |
| 3-Me-Rhamnose | 4.2 | 2,3-Rhamnose | 4.9 |
| 3-Me-Xylose | 4.2 | T-Xylose (pyranose) | 4.8 |
| 4-Me-Rhamnose | 3.9 | 4,6-Galactose | 4.3 |
| Glucose | 3.6 | T-Rhamnose | 4.2 |
| Mannose | 2.4 | 3,4-Fucose | 3.1 |
| Galacturonic acid | 2.0 | 3,4-Galacturonic Acid | 2.4 |
| 3-Me-Galactose | 2.0 | 2-Mannose/3-Mannose | 2.2 |
| Arabinose | 1.8 | 4-Fucose | 2.2 |
| amino sugar | 1.5 | T-Fucose | 2.2 |
| 2,3-diMe-Fucose | 1.2 | 3,4-Rhamnose | 2.1 |
| N-Acetyl Glucosamine | 0.9 | 2-Glucose | 1.5 |
| 2-Me-Glucose | 0.5 | 2,3-Mannose | 1.4 |
| Glycerol | 0.4 | 3-Glucose | 1.2 |
|  |  | 3-Galactose | 1.1 |
|  |  | 4-Mannose | 1.0 |
|  |  | 6-Mannose | 0.8 |
|  |  | 2,6-Glucose/4,6-Glucose | 0.8 |
|  |  | 3-Xylose | 0.7 |
|  |  | 4-Xylose | 0.6 |

Note: Methyl groups are represented by "Me" and terminal glycosyl linkages are represented by "T". All glycosyl linkages are also 1-linked unless otherwise specified. Presence of two glycosyl units indicates co-elution of components during analysis.

TABLE 4

The influence of temperature and ethanol concentration used during the initial extraction of AFA on percent recovery and specific activity of NP16847 polysaccharide preparation.

| Temperature | Percent ethanol concentration | | | | |
| --- | --- | --- | --- | --- | --- |
|  | 30% EtOH | 40% EtOH | 50% EtOH | 60% EtOH | 70% EtOH |
| 80° C. | 11.9 | 12.6 | 11.7 | 11.2 | 7.6 |
|  | 75 ng/mL | 50 ng/mL | 25 ng/mL | 25 ng/mL | 50 ng/mL |
| 70° C. | 11.0 | 11.1 | 10.2 | 10.0 | 7.1 |
|  | 75 ng/mL | 50 ng/mL | 25 ng/mL | 50 ng/mL | 75 ng/mL |
| 60° C. | 10.5 | 10.8 | 10.8 | 9.5 | 7.1 |
|  | 100 ng/mL | 50 ng/mL | 25 ng/mL | 100 ng/mL | 100 ng/mL |
| 50° C. | 10.9 | 10.3 | 9.4 | 9.4 | 6.5 |
|  | 100 ng/mL | 100 ng/mL | 75 ng/mL | 100 ng/mL | 100 ng/mL |
| 40° C. | 13.8 | 10.7 | 8.9 | 8.4 | 5.7 |
|  | 100 ng/mL | 100 ng/mL | 100 ng/mL | 200 ng/mL | 200 ng/mL |
| 23° C. | 13.7 | 11.4 | 9.1 | 7.0 | 4.5 |
|  | 200 ng/mL | >250 ng/mL | 200 ng/mL | >250 ng/mL | >250 ng/mL |

Legend
xx.x Percent recovery
XXng/mL $EC_{50}$ value

TABLE 5

Glycosyl composition analysis of different NP16847 preparations isolated from AFA. Data obtained from one experiment.

| NP16847 Preparation | NP7 | NP4 | NP6 | NP3 | NP5 | NP1 | NP2 | NP8 | NP9 |
|---|---|---|---|---|---|---|---|---|---|
| EC$_{50}$ value (ng/mL) | 10 | 20 | 20 | 25 | 25 | 100 | 500 | 500 | 500 |
| Glycosyl Residue | | | | | Mole % | | | | |
| Arabinose | 3.1 | 10.8 | 8.4 | 9.3 | 7.8 | 4.3 | 15.7 | 2.6 | 4.2 |
| Rhamnose | 15.8 | 12.8 | 11.8 | 14.4 | 12.0 | 12.4 | 19.0 | 5.1 | 5.5 |
| Fucose | 0.8 | 2.1 | 1.3 | 0.6 | 1.1 | 6.8 | 3.0 | 1.3 | 1.8 |
| Xylose | 0.8 | 1.3 | 1.0 | 0.9 | 0.8 | 2.2 | 1.4 | 0.7 | 1.0 |
| Glucuronic acid | 2.9 | 1.1 | 1.5 | 2.3 | 1.9 | 2.8 | 0.3 | — | — |
| Methylated Residues | 7.7 | 7.5 | 5.1 | 6.2 | 7.2 | 12.5 | 8.7 | 10.4 | 12.0 |
| Mannose | 33.2 | 22.1 | 24.9 | 29.7 | 24.0 | 19.9 | 5.1 | 9.0 | 9.3 |
| Galactose | 6.3 | 2.8 | 3.6 | 4.8 | 4.1 | 6.9 | 0.8 | 2.1 | 2.2 |
| Glucose | 9.8 | 5.7 | 8.0 | 21.0 | 15.8 | 9.0 | 2.9 | 60.8 | 56.5 |
| N-acetyl glucosamine | 4.2 | 3.5 | 4.6 | — | 4.3 | 4.5 | 1.2 | 3.5 | 2.7 |
| N-acetyl galactosamine | 5.5 | 10.8 | 11.5 | — | 7.5 | 8.6 | 15.6 | 1.4 | 1.5 |
| N-acetylated sugar | — | — | — | — | — | — | — | 3.1 | 3.3 |
| Unknown sugar (1) | 5.5 | 10.4 | 9.1 | 8.8 | 7.5 | 4.2 | 13.7 | — | — |
| Unknown sugar (2) | 0.4 | 1.1 | 0.8 | 0.6 | 0.7 | 3.3 | 1.9 | — | — |
| Unknown sugar (3) | 2.6 | 8.0 | 8.4 | 1.4 | 5.3 | 2.6 | 10.7 | — | — |
| Galacturonic acid | 1.4 | — | — | — | — | — | — | — | — |

1 = Example 1 NP16847 (post-ultrafiltrate), extraction with 70% ethanol at 40° C.
2 = New AFA batch NP16847 (post-ultrafiltrate), Example 1 conditions
3 = Pre-ultrafiltrate NP16847, extraction with 50% ethanol at 60° C. (Example 24)
4 = Post-ultrafiltrate NP16847, extraction with 50% ethanol at 60° C. (Example 24)
5 = Pre-ultrafiltrate NP16847, extraction with 50% ethanol at 70° C. (Example 25)
6 = Post-ultrafiltrate NP16847, extraction with 50% ethanol at 70° C. (Example 25)
7 = Marc material from extraction with 70% ethanol at 40° C., NP16847 (post-ultrafiltrate) re-extracted with 50% ethanol at 60° C. (Example 44)
8 = Pre-ultrafiltrate material, extraction with 100% water at 95° C. (Example 40)
9 = Post-ultrafiltrate material, extraction with 100% water at 95° C. (Example 40)

What is claimed is:

1. An immunostimulatory *Aphanizomenon flos-aquae* preparation isolated from *Aphanizomenon flos-aquae*, wherein the preparation is isolated by extraction of the *Aphanizomenon flos-aquae* with a solvent comprising a mixture of water and alcohol, and wherein said preparation comprises one or more immunostimulatory *Aphanizomenon flos-aquae* polysaccharides having an apparent molecular weight above approximately 2 million Daltons and wherein the glycosyl components of the immunostimulatory *Aphanizomenon flos-aquae* polysaccharides are comprised of mannose, glucose, rhamnose, galactose, fucose, methylated sugars and N-acetylated amino sugars.

2. The immunostimulatory preparation of claim 1 wherein the immunostimulatory activity is manifested by monocyte/macrophage activation.

3. A pharmaceutical composition comprising the immunostimulatory preparations of claim 2 and a pharmaceutically acceptable carrier or excipient.

4. A dietary supplement comprising the immunostimulatory preparations of claim 2 and an acceptable carrier or excipient for dietary supplements.

5. A pharmaceutical composition comprising the immunostimulatory preparations of claim 1 and a pharmaceutically acceptable carrier or excipient.

6. A dietary supplement comprising the immunostimulatory preparations of claim 1 and an acceptable carrier or excipient for dietary supplements.

7. An immunostimulatory *Chlorella* preparation isolated from *Chlorella*, wherein the preparation is isolated by extraction of the *Chlorella* with a solvent comprising a mixture of water and alcohol, and wherein said preparation comprises one or more immunostimulatory *Chlorella* polysaccharides having an apparent molecular weight above approximately 2 million Daltons and wherein the glycosyl components of the immunostimulatory *Chlorella* polysaccharides are comprised of arabinose, galactose, rhamnose, glucose and methylated sugars.

8. The immunostimulatory preparation of claim 7 wherein the immunostimulatory activity is manifested by monocyte/macrophage activation.

9. A pharmaceutical composition comprising the immunostimulatory preparations of claim 8 and a pharmaceutically acceptable carrier or excipient.

10. A dietary supplement comprising the immunostimulatory preparations of claim 8 and an acceptable carrier or excipient for dietary supplements.

11. The immunostimulatory preparation of claim 7 wherein the microalgae are those of *Chlorella pyrenoidosa*.

12. A pharmaceutical composition comprising the immunostimulatory preparations of claim 11 and a pharmaceutically acceptable carrier or excipient.

13. A pharmaceutical composition comprising the immunostimulatory preparations of claim 7 and a pharmaceutically acceptable carrier or excipient.

14. A dietary supplement comprising the immunostimulatory preparations of claim 7 and an acceptable carrier or excipient for dietary supplements.

15. An immunostimulatory *Spirulina* preparation isolated from *Spirulina*, wherein the preparation is isolated by extraction of the *Spirulina* with a solvent comprising a mixture of water and alcohol, and wherein said preparation comprises one or more immunostimulatory *Spirulina* polysaccharides having an apparent molecular weight above approximately 2 million Daltons and wherein the glycosyl components of the immunostimulatory *Spirulina* polysaccharides are comprised of rhamnose, glucuronic acid, fucose, galactose and methylated sugars.

16. The immunostimulatory preparation of claim 15 wherein the immunostimulatory activity is manifested by monocyte/macrophage activation.

17. A pharmaceutical composition comprising the immunostimulatory preparations of claim 16 and a pharmaceutically acceptable carrier or excipient.

18. A dietary supplement comprising the immunostimulatory preparations of claim 16 and an acceptable carrier or excipient for dietary supplements.

19. The immunostimulatory preparation of claim 15 wherein the microalgae are those of *Spirulina platensis*.

20. A pharmaceutical composition comprising the immunostimulatory preparations of claim 19 and a pharmaceutically acceptable carrier or excipient.

21. A pharmaceutical composition comprising the immunostimulatory preparations of claim 15 and a pharmaceutically acceptable carrier or excipient.

22. A dietary supplement comprising the immunostimulatory preparations of claim 15 and an acceptable carrier or excipient for dietary supplements.

* * * * *

UNITED STATES PATENT AND TRADEMARK OFFICE
CERTIFICATE OF CORRECTION

PATENT NO. : 7,205,284 B2
APPLICATION NO. : 10/332323
DATED : April 17, 2007
INVENTOR(S) : D. Pasco et al.

It is certified that error appears in the above-identified patent and that said Letters Patent is hereby corrected as shown below:

Title Page 1, first column, item (75), change "Nala Miazi ElSohly" to --Hala Niazi ElSohly--;

Title Page 1, first column, item (60), change "Jul. 10, 2001" to --Jul. 10, 2000--.

Signed and Sealed this

Fifteenth Day of May, 2007

JON W. DUDAS
*Director of the United States Patent and Trademark Office*